(12) United States Patent
Degenhardt et al.

(10) Patent No.: US 6,809,093 B2
(45) Date of Patent: Oct. 26, 2004

(54) 2-SUBSTITUTED HETEROCYCLIC COMPOUNDS

(75) Inventors: Charles Raymond Degenhardt, Cincinnati, OH (US); David Joseph Eickhoff, Edgewood, KY (US)

(73) Assignee: H. Lee Moffitt Cancer & Research Institute, Inc., Tampa, FL (US)

( * ) Notice: Subject to any disclaimer, the term of this patent is extended or adjusted under 35 U.S.C. 154(b) by 0 days.

(21) Appl. No.: 09/741,272

(22) Filed: Dec. 19, 2000

(65) Prior Publication Data

US 2002/0119960 A1 Aug. 29, 2002

Related U.S. Application Data

(60) Provisional application No. 60/241,127, filed on Oct. 17, 2000.

(51) Int. Cl.[7] .................. C07D 401/12; C07D 401/14; A61K 31/4709; A61K 31/4545; A61P 35/00

(52) U.S. Cl. ........................ 514/217.04; 514/253.06; 514/253.07; 514/253.13; 514/311; 514/312; 514/314; 514/316; 514/317; 514/318; 514/326; 540/481; 540/597; 544/360; 544/363; 544/364; 546/153; 546/189; 546/193; 546/208

(58) Field of Search .................... 514/217.04, 253.06, 514/253.07, 253.13, 311, 312, 314, 316, 318, 326, 317; 540/481, 597; 544/360, 363, 364; 546/153, 189, 193, 208, 174, 194, 175, 209

(56) References Cited

U.S. PATENT DOCUMENTS

| | | | | |
|---|---|---|---|---|
| 5,506,239 A | * | 4/1996 | Sato et al. | ................ 514/312 |
| 5,736,539 A | * | 4/1998 | Graham et al. | ............ 514/218 |

FOREIGN PATENT DOCUMENTS

| | | | |
|---|---|---|---|
| DE | 195 48 797 A1 | * | 7/1997 |
| JP | 09 12577 | | 1/1997 |
| WO | WO 92/18478 A1 | | 10/1992 |
| WO | WO 93/04042 A1 | * | 3/1993 |
| WO | WO 94/07856 A1 | | 4/1994 |
| WO | WO 97/26240 A1 | * | 7/1997 |
| WO | WO 99/65867 A1 | * | 12/1999 |
| WO | WO 00/01714 A1 | | 1/2000 |
| WO | WO 00/32588 A2 | | 6/2000 |
| WO | WO 00/37458 A1 | * | 6/2000 |
| WO | WO 00/50418 A1 | | 8/2000 |
| WO | WO 01/58891 A2 | | 8/2001 |
| WO | WO 01/74769 A1 | | 10/2001 |

OTHER PUBLICATIONS

Vicar, J.; Smolikova, Jorga; Blaha, Karel, Collect. Czech. Chem. Commun., 37(12), 4060–71, (English) 1972.*
Balaspiri, L.; Papp, G. Y.; Pallai, P.; Kovacs, K, Acta Phys. Chem., 20(1–2), 105–10 (English) 1974.*
Kovacs, Gabor L.; Szabo, Gyula; Telegdy, Gyula; Balaspiri, Lajos; Palos, Eva; Szpornyi, Laszlo, Pharmacol., Biochem. Behav., 31(4), 833–7 (English) 1988.*
Martin, Juliette; Lasne, Marie–Claire; Plaquevent, Jean–Christophe; Duhamel, Lucette, Tetrahedron Lett., 38(41), 7181–7182 (English) 1997.*
U.S. patent application Ser. No. 09/740,642, Degenhardt, filed Dec. 19, 2000.
U.S. patent application Ser. No. 09/741,588, Degenhardt, filed Dec. 19, 2000.
U.S. patent application Ser. No. 09/740,644, Degenhardt, filed Dec. 19, 2000.
U.S. patent application Ser. No. 09/740,387, Degenhardt, filed Dec. 19, 2000.
U.S. patent application Ser. No. 09/740,643, Degenhardt, filed Dec. 19, 2000.
U.S. patent application Ser. No. 09/740,388, Degenhardt, filed Dec. 19, 2000.
U.S. patent application Ser. No. 09/740,391, Degenhardt, filed Dec. 19, 2000.
U.S. patent application Ser. No. 09/740,279, Degenhardt, filed Dec. 19, 2000.

* cited by examiner

*Primary Examiner*—Thomas McKenzie
(74) *Attorney, Agent, or Firm*—Michael Best & Friedrich, LLP

(57) ABSTRACT

Compounds, compositions, and methods for treating multi-drug resistance are disclosed. Suitable compounds are 2-substituted heterocyclic compounds. An example compound has the formula:

4 Claims, No Drawings

2-SUBSTITUTED HETEROCYCLIC COMPOUNDS

CROSS REFERENCE

This application claims priority under 35 U.S.C. § 120 to Provisional Application Ser. No. 60/241,127 filed on Oct. 17, 2000.

FIELD OF THE INVENTION

This invention relates to compounds for treating multidrug resistance and methods for their preparation and use. More particularly, this invention relates to compounds that regulate the cellular transport proteins P-glycoprotein or MRP1, or both, which are the proteins believed to be largely responsible for causing multidrug resistance in cancer patients.

BACKGROUND OF THE INVENTION

"Drug resistance" means a circumstance when a disease (e.g., cancer) does not respond to a therapeutic agent. Drug resistance can be intrinsic, which means that the disease has never been responsive to the therapeutic agent, or acquired, which means that the disease ceases responding to the agent or agents to which the disease had previously been responsive. "Multidrug resistance" is a type of drug resistance wherein a disease is resistant to a variety of drugs that can be functionally unrelated, structurally unrelated, or both. Multidrug resistance is a problem associated with cancer and other conditions, such as bacterial, viral, protozoal, and fungal diseases.

One cause of multidrug resistance in cancer patients is that many cancer cells express high levels of the transmembrane transport proteins, such as Pleiotropic-glycoprotein (also known as Pgp, P-glycoprotein, gp-170, or MDR1) and MRP1 (see Borst, P., "Multidrug resistance: A solvable problem?" *Annals of Oncology*, 10, suppl. 4, pp. S162–S164 (1999)). In adenosine-triphosphate driven processes, these transport proteins export hydrophobic compounds (such as vinblastine, daunorubicin, doxorubicin, etoposide, vincristine, and TAXOL®, which are cytotoxic drugs useful for treating cancer) from the cell in an effort to protect the cell from harm. The transport proteins remove the compounds from the cell prior to their having a lethal effect on the cell (see Legrand, et. al, "Simultaneous Activity of MRP1 and Pgp Is Correlated With In Vitro Resistance to Daunorubicin and With In Vivo Resistance in Adult Acute Myeloid Leukemia", *Blood, Vol.* 94, No. 3, pp. 1046–1056 (1999); and Zhu, B. T.; "A Novel Hypothesis for the Mechanism of Action of P-glycoprotein as a Multidrug Transporter," *Molecular Carcinogenesis* 25, pp. 1–14 (1999)). Although it is not currently known which of these two classes of proteins is more important for multidrug resistance, and indeed it may be that the class (or classes) of protein which is important depends on the type of cancer and the particular drug or drugs used to treat the cancer, Pgp is known to be highly expressed in approximately 50% of human cancers which require drug therapy. Consequently, Pgp is believed to be a major cause of multidrug resistance.

Other types of multidrug resistance, such as antibacterial, antiviral, and antifungal multidrug resistance may also be caused by the action of transport proteins that are similar to Pgp, and others (see "Annual Reports on Medicinal Chemistry—33; Section III Cancer and Infectious Diseases" ed. Plattner, J., Academic Press, Ch. 12, pp. 121–130 (1998)).

Furthermore, Pgp is also expressed at high levels in the gastrointestinal tract, liver, kidneys, and brain, and therefore Pgp represents a major pharmacological barrier to the bioavailability of many drugs (see Amudkar, et. al in "Biochemical, Cellular, and Pharmacological Aspects of the Multidrug Transporter," *Annu. Rev. Pharmacol. Toxicol.*, 39, pp. 361–398 (1999)). For example, the oral bioavailability of many nutrients and drugs is negatively affected by the action of Pgp present in the gastrointestinal tract. "Oral bioavailability" means the ability of a drug or nutrient that is administered orally to be transported across the gastrointestinal tract and enter into the bloodstream. In addition, Pgp adversely affects penetration of many drugs through the blood-brain barrier.

SUMMARY OF THE INVENTION

This invention relates to novel compounds useful in treating or preventing multidrug resistance ("MDR"). More specifically, these compounds are useful in treating or preventing P-glycoprotein-mediated MDR and MRP1-mediated MDR. This invention further relates to compositions comprising these compounds. This invention further relates to methods for the preparation and use of the compounds and compositions. The compounds and compositions of this invention are well suited for treatment of multidrug resistant cells, for prevention of the development of multidrug resistance, and for use in multidrug resistant chemotherapies.

DETAILED DESCRIPTION OF THE INVENTION

Publications and patents are referred to throughout this disclosure. All U.S. Patents cited herein are hereby incorporated by reference.

All percentages, ratios, and proportions used herein are by weight unless otherwise specified.

Definitions and Usage of Terms

The following is a list of definitions, as used herein.

"Aromatic group" means a group having a monocyclic or polycyclic ring structure. Monocyclic aromatic groups contain 4 to 10 carbon atoms, preferably 4 to 7 carbon atoms, and more preferably 4 to 6 carbon atoms in the ring. Preferred polycyclic ring structures have two or three rings. Polycyclic structures having two rings typically have 8 to 12 carbon atoms, preferably 8 to 10 carbon atoms in the rings. Polycyclic aromatic groups include groups wherein at least one, but not all, of the rings are aromatic.

"Carbocyclic group" means a saturated or unsaturated hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups contain 4 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the rings.

"Carrier" means one or more substances that are suitable for administration to a subject (i.e., mammal) and that can be combined with the active compound according to this invention. Carrier includes solid and liquid diluents, hydrotropes, surface-active agents, and encapsulating substances.

"Chemosensitizing agent" means a noncytotoxic compound that sensitizes drug resistant cells to the action of cytotoxic drugs. As used in this application, the term "chemosensitizing agent", excludes the active compounds of this invention.

"Halogen atom" means F, Cl, Br, or I.

"Heteroaromatic group" means an aromatic group containing carbon and 1 to 4 heteroatoms in the ring. Monocyclic heteroaromatic groups contain 4 to 10 member atoms, preferably 4 to 7 member atoms, and more preferably 4 to 6 member atoms in the ring. Preferred polycyclic ring structures have two or three rings. Polycyclic structures having two rings typically have 8 to 12 member atoms, preferably 8 to 10 member atoms in the rings. Polycyclic heteroaromatic groups include groups wherein at least one, but not all, of the rings are heteroaromatic.

"Heteroatom" means an atom selected from the group consisting of sulfur, phosphorous, nitrogen, and oxygen, e.g., in the ring of a heterocyclic group or the chain of a heterogeneous group. Groups containing more then one heteroatom may contain different heteroatoms.

"Heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), preferably 4 to 7, and more preferably 5 to 6 in the ring. Bicyclic heterocyclic groups contain 8 to 18 member atoms, preferably 9 or 10 in the rings.

"Heterogeneous group" means a saturated or unsaturated chain of non-hydrogen member atoms comprising carbon atoms and at least one heteroatom. Heterogeneous groups typically have 1 to 25 member atoms. Preferably, the chain contains 1 to 12 member atoms, more preferably 1 to 10, and most preferably 1 to 6. The chain may be linear or branched. Preferred branched heterogeneous groups have one or two branches, preferably one branch. Preferred heterogeneous groups are saturated. Unsaturated heterogeneous groups have one or more double bonds, one or more triple bonds, or both. Preferred unsaturated heterogeneous groups have one or two double bonds or one triple bond. More preferably, the unsaturated heterogeneous group has one double bond.

"Hydrocarbon group" means a chain of 1 to 25 carbon atoms, preferably 1 to 12 carbon atoms, more preferably 1 to 10 carbon atoms, and most preferably 1 to 8 carbon atoms. Hydrocarbon groups may have a linear or branched chain structure. Preferred hydrocarbon groups have one or two branches, preferably 1 branch. Preferred hydrocarbon groups are saturated. Unsaturated hydrocarbon groups have one or more double bonds, one or more triple bonds, or combinations thereof. Preferred unsaturated hydrocarbon groups have one or two double bonds or one triple bond; more preferred unsaturated hydrocarbon groups have one double bond.

"$IC_{50}$" means concentration of drug required to produce a 50% inhibition of growth of cancer cells or 50% inhibition of activity.

"MDR" means multidrug resistance.

"Parenteral" as used herein includes subcutaneous, intravenous, intramuscular, intraarticular, intrasynovial, intrastemal, intrathecal, intrahepatic, intralesional and intracranial injection or infusion techniques.

"Pgp" means P-glycoprotein.

"Pharmaceutically acceptable" means suitable for use in a human or other mammal.

"Protecting group" is a group that replaces the active hydrogen of a —OH, —COOH, or —$NH_2$ moiety thus preventing undesired side reaction at the moiety. Use of protecting groups in organic synthesis is well known in the art. Examples of protecting groups are found in *Protecting Groups in Organic Synthesis* by Greene, T. W. and Wuts, P. G. M., 2nd ed., Wiley & Sons, Inc., 1991. Preferred protecting groups for hydroxyl moieties include silyl ethers, alkoxymethyl ethers, tetrahydropyranyl, tetrahydrofaranyl, esters, and substituted or unsubstituted benzyl ethers. Other preferred protecting groups include carbamates.

"Subject" means a living vertebrate animal such as a mammal (preferably human).

"Substituted aromatic group" means an aromatic group wherein 1 or more of the hydrogen atoms bonded to carbon atoms in the ring have been replaced with other substituents. Preferred substituents include hydrocarbon groups such as methyl groups and heterogeneous groups including alkoxy groups such as methoxy groups. The substituents may be substituted at the ortho, meta, or para position on the ring, or any combination thereof.

"Substituted carbocyclic group" means a carbocyclic group wherein 1 or more hydrogen atoms bonded to carbon atoms in the ring have been replaced with other substituents. Preferred substituents include hydrocarbon groups such as alkyl groups (e.g., methyl groups) and heterogeneous groups such as alkoxy groups (e.g., methoxy groups).

"Substituted heteroaromatic group" means a heteroaromatic group wherein 1 or more hydrogen atoms bonded to carbon atoms in the ring have been replaced with other substituents. Preferred substituents include monovalent hydrocarbon groups including alkyl groups such as methyl groups and monovalent heterogeneous groups including alkoxy groups such as methoxy groups.

"Substituted heterocyclic group" means a heterocyclic group wherein 1 or more hydrogen atoms bonded to carbon atoms in the ring have been replaced with other substituents. Preferred substituents include monovalent hydrocarbon groups including alkyl groups such as methyl groups and monovalent heterogeneous groups including alkoxy groups such as methoxy groups. Substituted heterocyclic groups are not aromatic.

"Substituted heterogeneous group" means a heterogeneous group, wherein 1 or more of the hydrogen atoms bonded to carbon atoms in the chain have been replaced with other substituents. Preferred substituents include monovalent hydrocarbon groups including alkyl groups such as methyl groups and monovalent heterogeneous groups including alkoxy groups such as methoxy groups.

"Substituted hydrocarbon group" means a hydrocarbon group wherein 1 or more of the hydrogen atoms bonded to carbon atoms in the chain have been replaced with other substituents. Preferred substituents include monovalent aromatic groups, monovalent substituted aromatic groups, monovalent hydrocarbon groups including alkyl groups such as methyl groups, monovalent substituted hydrocarbon groups such as benzyl, and monovalent heterogeneous groups including alkoxy groups such as methoxy groups.

"Substrate potential" means the likelihood that a compound for use in treating multidrug resistance will be transported out of a cell by cellular transport proteins before effectively preventing or reversing multidrug resistance.

"Transport protein" means a protein that acts to remove cytotoxic substances from cells through the cell membrane. Transport protein includes P-glycoprotein, MRP1, and others.

"Treating multidrug resistance" means preventing multidrug resistance from developing in nonresistant cells, increasing or restoring sensitivity of multidrug resistant cells to therapeutic or prophylactic agents, or both.

"Treating" means 1) preventing a disease (i.e., causing the clinical symptoms of the disease not to develop), 2) inhibiting the disease (i.e., arresting the development of clinical symptoms of the disease), 3) relieving the disease (i.e., causing regression of the clinical symptoms), and combinations thereof.

"Wax" means a lower-melting organic mixture or compound of high molecular weight, solid at room temperature and generally similar in formulation to fats and oils except that they contain no glycerides.

Active Compounds Used in this Invention

The active compounds can have the structure:

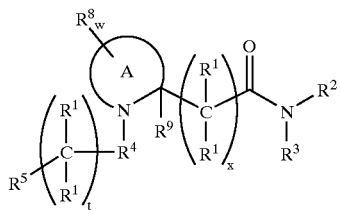

wherein w is 0 to about 6, x is 0 to about 10, and t is 0 to about 6. Preferably x is 0. Preferably, t is 0 to about 3.

$R^1$ is selected from the group consisting of a hydrogen atom, a hydroxyl group, a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group. Preferably, $R^1$ is selected from the group consisting of a hydrogen atom and a hydroxyl group.

$R^2$ and $R^3$ are bonded together to form a substituted heterocyclic group having about 4 to about 9 members in the ring, preferably about 5 to about 6 members. In a preferred embodiment of the invention, the substituted heterocyclic group is substituted with a group selected from the group consisting of an aromatic group; a substituted aromatic group; a heteroaromatic group; a substituted heteroaromatic group; a substituted hydrocarbon group, wherein the substituted hydrocarbon group is substituted with a group selected from the group consisting of an aromatic group, a substituted aromatic group, a heteroaromatic group, and a substituted heteroaromatic group; and a substituted heterogenous group, wherein the substituted heterogenous group is substituted with a group selected from the group consisting of an aromatic group, a substituted aromatic group, a heteroaromatic group, and a substituted heteroaromatic group.

The substituted heterocyclic optionally contains 1 or more members selected from the group consisting of O, and $NR^{10}$, wherein $R^{10}$ is selected from the group consisting of hydrogen atom, a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group. Suitable substituted hydrocarbon groups for $R^{10}$ include methylenyl-diphenyl. Suitable substituted aromatic groups for $R^{10}$ include phenylmethyl and phenylmethoxy. Suitable heteroaromatic groups for $R^{10}$ include pyridyl.

Suitable substituted heterogenous groups for $R^{10}$ have the formula —$(CR^1{}_2)_w$—$D^1$—$O_y$—$D^2{}_z$—$R^{15}$, wherein w is 0 to about 6, y is 0 or 1, z is 0 or 1. Preferably, w and y are both 0.

$R^{15}$ is selected from the group consisting of a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group. $R^{15}$ is preferably selected from the group consisting of

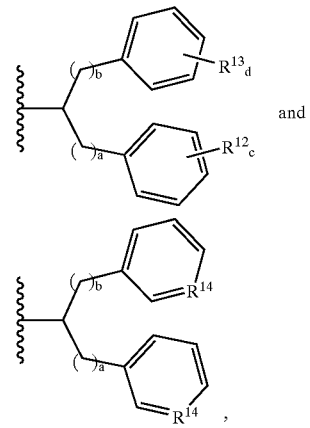

wherein
wherein a is at least about 2, b is at least about 2, c is about 1 to about 3, and d is about 1 to about 3. Preferably, a and b are each about 3 to about 10. More preferably, a and b are each about 3.

$R^{12}$ and $R^{13}$ are each independently selected from the group consisting of hydrocarbon groups and substituted hydrocarbon groups. Preferably, $R^{12}$ and $R^{13}$ are substituted hydrocarbon groups such as alkoxy groups. Preferred alkoxy groups include methoxy, ethoxy, propoxy, and butoxy.

Each $R^{14}$ is independently selected from the group consisting of CH and a heteroatom. Preferably, the heteroatom is nitrogen. More preferably, each $R^{14}$ is CH.

$D^1$ and $D^2$ are each independently selected from the group consisting of —C(O)— and —$NR^{16}$—, wherein $R^{16}$ is selected from the group consisting of a hydrogen atom and $R^{15}$.

The substituted heterocyclic group formed by $R^2$ and $R^3$ is preferably a substituted piperidyl or substituted piperazinyl.

$R^4$ is selected from the group consisting of —$S(O)_2$—, —C(O)—, —C(O)—C(O)—, and —$CH(R^1)$—.

$R^5$ is selected from the group consisting of —$NR^6(R^7)$ and —$O_rR^6$, wherein r is 0 or 1. Preferably, $R^5$ is —$O_rR^6$.

$R^6$ is selected from the group consisting of a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group. Preferably, $R^6$ is selected from the group consisting of an aromatic group, a substituted aromatic group, a heteroaromatic group, and a substituted heteroaromatic group.

In a preferred embodiment of the invention, $R^6$ is a heteroaromatic group of the formula:

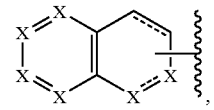

wherein each X is independently selected from the group consisting of CH and a heteroatom, with the proviso that at least one X is a heteroatom. The heteroatom is preferably nitrogen. Preferably, one X is a heteroatom. Examples of heteroaromatic groups for $R^6$ include quinolyl and isoquinolyl groups. Preferred quinolyl groups for $R^6$ include 4-quinolyl, 5-quinolyl, 6-quinolyl, 7-quinolyl, and 8-quinolyl. More preferably, $R^6$ is 5-quinolyl.

$R^7$ is selected from the group consisting of a hydrogen atom and $R^6$.

Preferred compounds wherein $R^4$ is —S(O)$_2$— and $R^5$ is —O$_r$R$^6$ are shown below in Table 1.

TABLE 1

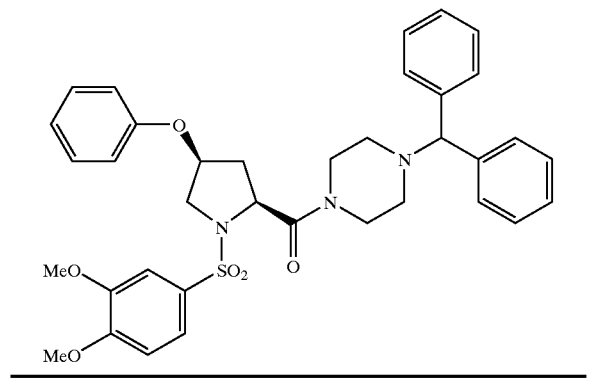

Preferred compounds wherein $R^4$ is —C(O)— and $R^5$ is —O$_r$R$^6$ are shown below in Table 2.

TABLE 2

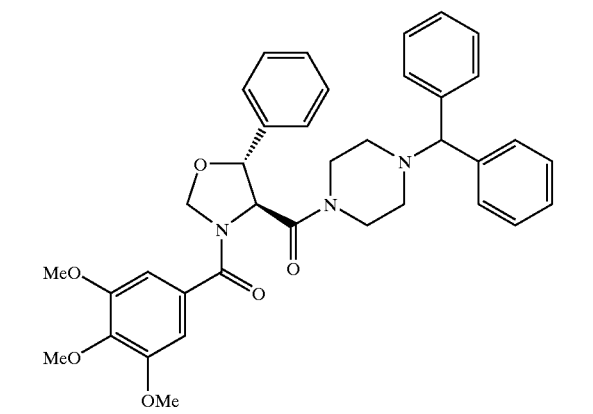

Preferred compounds wherein $R^4$ is —C(O)—C(O)— and $R^5$ is —O$_r$R$^6$ are shown below in Table 3.

TABLE 3

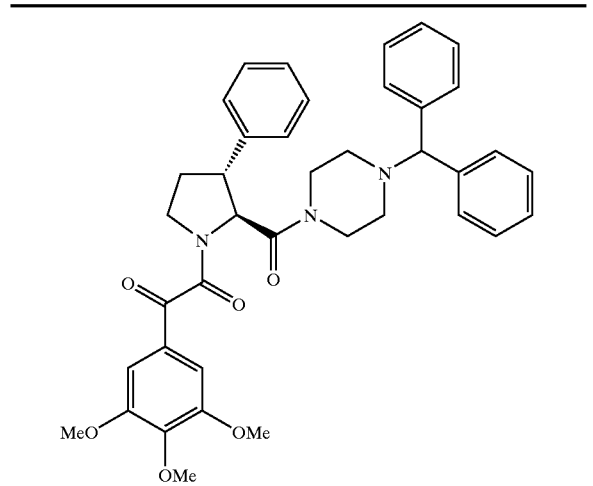

TABLE 3-continued

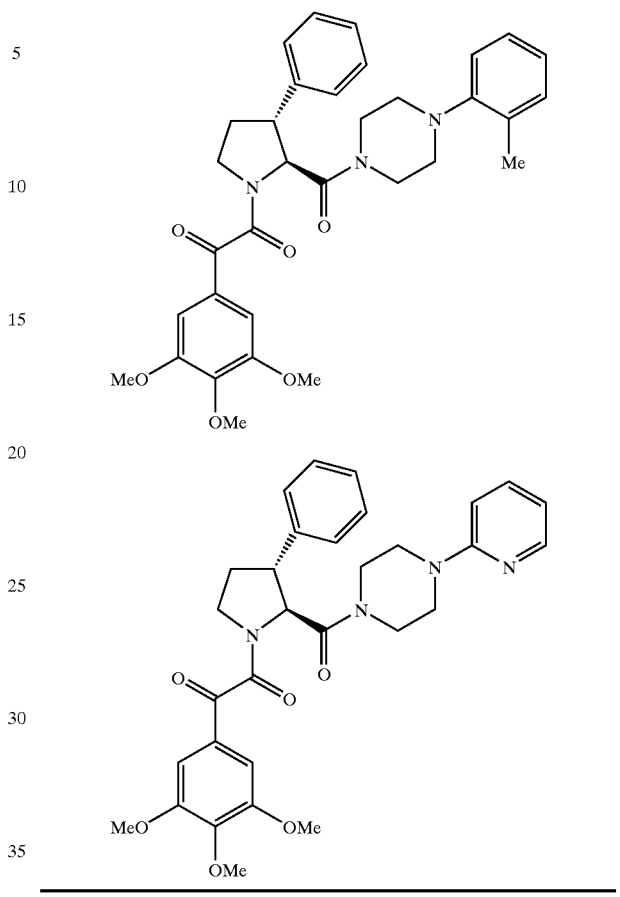

Preferred compounds wherein $R^4$ is —CH(R$^1$)— and $R^5$ is —O$_r$R$^6$ are shown below in Table 4.

TABLE 4

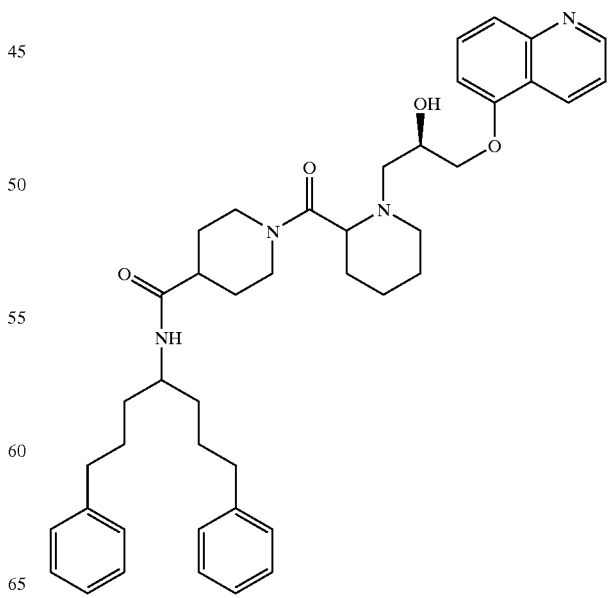

TABLE 4-continued

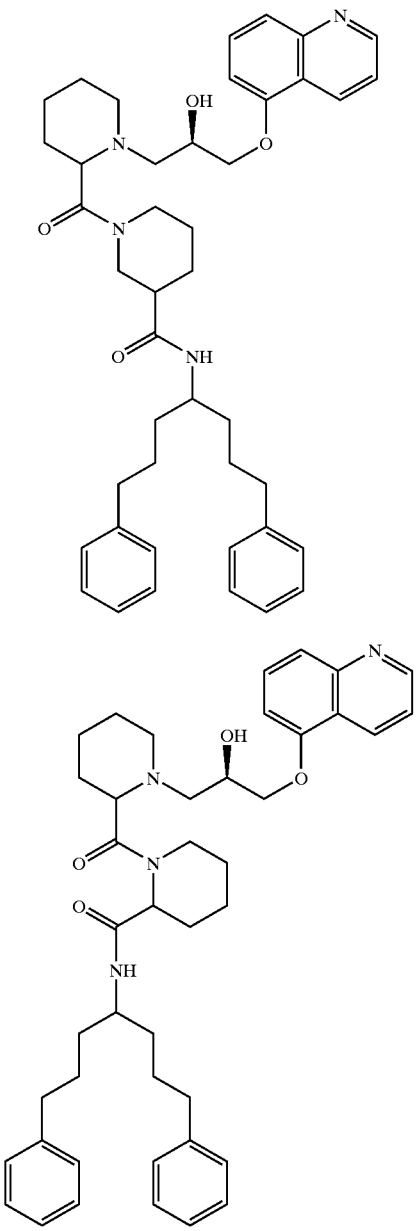

R⁸ is selected from the group consisting of a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group.

R⁹ is selected from the group consisting of a hydrogen atom and a hydrocarbon group.

A is a substituted heterocyclic group having about 4 to about 9 members. Preferably, A has about 4 to about 7 members. More preferably, A has about 5 to about 6 members. A may contain one or more additional heteroatoms selected from the group consisting of O and S, preferably O. A contains only one nitrogen atom.

In an alternative embodiment of the invention, the compound can be an optical isomer, a diastereomer, an enantiomer, a pharmaceutically-acceptable salt, a biohydrolyzable amide, a biohydrolyzable ester, or a biohydrolyzable imide of the structure; or combinations thereof.

The active compound of this invention inhibits at least one transport protein. The active compound preferably inhibits Pgp or MRP1. More preferably, the active compound inhibits both Pgp and MRP1. In a preferred embodiment of this invention, the active compound inhibits Pgp and has low substrate potential for Pgp. In an alternative preferred embodiment, the active compound inhibits MRP1 and has low substrate potential for MRP1. In the most preferred embodiment of this invention, the active compound inhibits both Pgp and MRP1 and the active compound has low substrate potential for both Pgp and MRP1.

The degree to which a compound inhibits a transport protein can be measured by quantitating the effectiveness of the compound toward restoring drug sensitivity to multidrug resistant cells. Methods for quantitating the effectiveness of the active compounds toward restoring drug sensitivity are readily available to one skilled in the art without undue experimentation (see U.S. Pat. Nos. 5,935,954 and 5,272,159, which are hereby incorporated by reference for the purpose of disclosing these methods). Any assay known to measure the restoration of the anti-proliferative activity of a drug may be employed to test the compounds of this invention. These assays use cell lines resistant to particular drugs, and characterized by the presence of one or both of Pgp and MRP1. These cell lines include L1210, HL60, P388, CHO, and MCF7. Alternatively, resistant cell lines can be developed by methods readily available to one of ordinary skill in the art without undue experimentation (see Chaudhary, et al., "Induction of Multidrug Resistance in Human Cells by Transient Exposure to Different Chemotherapeutic Agents," *Journal of the National Cancer Institute,* Vol. 85, No. 8, pp. 632–639 (1993)). The cell line is then exposed to compounds of this invention in the presence or absence of the drug to which it is resistant, such as TAXOL®. The viability of the cells treated with both the active compound and the drug can then be compared to the viability of the cells treated only with the drug.

The active compound preferably also has low substrate potential for Pgp or MRP1. More preferably, the active compound has low substrate potential for both Pgp and MRP1. Substrate potential for a transport protein can be determined by using an assay for measuring ATPase activity of the Pgp or MRP1 pumps (see, for example, Reference Example 4, below).

Methods for quantitating accumulation of the active compounds are readily available to one skilled in the art without undue experimentation (see U.S. Pat. No. 5,272,159 which is hereby incorporated by reference for the purpose of disclosing assays for quantitating accumulation). These assays use cell lines resistant to particular chemotherapeutic agents, and characterized by the presence of one or both of Pgp and MRP1. The cell line is exposed to a labeled form of the active compound (e.g., radioactivity or fluorescence labeling) and the accumulation of the active compound is monitored over time. The amount of active compound accumulated in the cell can be compared with a compound which is readily transported by these proteins, e.g. labeled taxol.

Compositions of this Invention

This invention further relates to a composition. The composition can be used for treating various conditions or disease states. The composition is preferably a pharmaceutical composition administered for treatment or prevention of multidrug resistance. Standard pharmaceutical formulation techniques are used, such as those disclosed in *Remington's Pharmaceutical Sciences,* Mack Publishing Company, Easton, Pa. (1990) and U.S. Pat. No. 5,091,187, which is hereby incorporated by reference.

The composition comprises component (A) the active compound described above and component (B) a carrier. The composition may further comprise component (C) an optional ingredient, such as a therapeutic agent.

Component (B) is a carrier. A carrier is one or more compatible substances that are suitable for administration to a mammal. "Compatible" means that the components of the composition are capable of being commingled with component (A), and with each other, in a manner such that there is no interaction which would substantially reduce the efficacy of the composition under ordinary use situations. Carriers must be of sufficiently high purity and sufficiently low toxicity to render them suitable for administration to the mammal being treated. The carrier can be inert, or it can possess pharmaceutical benefits, cosmetic benefits, or both, depending on the intended use as described herein.

The choice of carrier for component (B) depends on the route by which component (A) will be administered and the form of the composition. The composition may be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis).

Systemic Compositions

Carriers for systemic administration typically comprise one or more ingredients selected from the group consisting of a) diluents, b) lubricants, c) binders, d) disintegrants, e) colorants, f) flavors, g) sweeteners, h) antioxidants, j) preservatives, k) glidants, m) solvents, n) suspending agents, o) surfactants, combinations thereof, and others.

Ingredient a) is a diluent. Suitable diluents include sugars such as glucose, lactose, dextrose, and sucrose; polyols such as propylene glycol; calcium carbonate; sodium carbonate; glycerin; mannitol; sorbitol; and maltodextrin. The amount of ingredient a) in the composition is typically about 1 to about 99%.

Ingredient b) is a lubricant. Suitable lubricants are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of ingredient b) in the composition is typically about 1 to about 99%.

Ingredient c) is a binder. Suitable binders include polyvinylpyrrolidone; magnesium aluminum silicate; starches such as corn starch and potato starch; gelatin; tragacanth; and cellulose and its derivatives, such as sodium carboxymethylcellulose, ethylcellulose, methylcellulose, microcrystalline cellulose, and hydroxypropylmethylcellulose; carbomer; providone; acacia; guar gum; and xanthan gum. The amount of ingredient c) in the composition is typically about 1 to about 99%.

Ingredient d) is a disintegrant. Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of ingredient d) in the composition is typically about 1 to about 99%.

Ingredient e) is a colorant such as an FD&C dye. The amount of ingredient e) in the composition is typically about 1 to about 99%.

Ingredient f) is a flavor such as menthol, peppermint, and fruit flavors. The amount of ingredient f) in the composition is typically about 1 to about 99%.

Ingredient g) is a sweetener such as saccharin and aspartame. The amount of ingredient g) in the composition is typically about 1 to about 99%.

Ingredient h) is an antioxidant such as butylated hydroxyanisole, butylated hydroxytoluene, and vitamin E. The amount of ingredient h) in the composition is typically about 1 to about 99%.

Ingredient j) is a preservative such as phenol, alkyl esters of parahydroxybenzoic acid, benzoic acid and the salts thereof, boric acid and the salts thereof, sorbic acid and the salts thereof, chorbutanol, benzyl alcohol, thimerosal, phenylmercuric acetate and nitrate, nitromersol, benzalkonium chloride, cetylpyridinium chloride, methyl paraben, ethyl paraben, and propyl paraben. Particularly preferred are the salts of benzoic acid, cetylpyridinium chloride, methyl paraben and propyl paraben, and sodium benzoate. The amount of ingredient j) in the composition is typically about 1 to about 99%.

Ingredient k) is a glidant such as silicon dioxide. The amount of ingredient k) in the composition is typically about 1 to about 99%.

Ingredient m) is a solvent, such as water, isotonic saline, ethyl oleate, alcohols such as ethanol, glycerin, cremaphor, glycols (e.g., polypropylene glycol and polyethylene glycol), and buffer solutions (e.g., phosphate, potassium acetate, boric carbonic, phosphoric, succinic, malic, tartaric, citric, acetic, benzoic, lactic, glyceric, gluconic, glutaric, and glutamic). The amount of ingredient m) in the composition is typically about 1 to about 99%.

Ingredient n) is a suspending agent. Suitable suspending agents include AVICEL® RC-591 from FMC Corporation of Philadelphia, Pa. and sodium alginate. The amount of ingredient n) in the composition is typically about 1 to about 99%.

Ingredient o) is a surfactant such as lecithin, polysorbate 80, sodium lauryl sulfate, polyoxyethylene sorbitan fatty acid esters, polyoxyethylene monoalkyl ethers, sucrose monoesters, lanolin esters, and lanolin ethers. Suitable surfactants are known in the art and commercially available, e.g., the TWEENS® from Atlas Powder Company of Wilmington, Del. Suitable surfactants are disclosed in the *C.T.F.A. Cosmetic Ingredient Handbook,* pp.587–592 (1992); *Remington's Pharmaceutical Sciences,* 15th Ed., pp. 335–337 (1975); and *McCutcheon's Volume 1. Emulsifiers & Detergents,* North American Edition, pp. 236–239 (1994). The amount of ingredient o) in the composition is typically about 1 to about 99%.

The carrier ingredients discussed above are exemplary and not limiting. One skilled in the art would recognize that different carrier ingredients may be added to or substituted for the carrier ingredients above. One skilled in the art would be able to select appropriate carrier ingredients for systemic compositions without undue experimentation.

Compositions for parenteral administration typically comprise (A) about 0.1 to about 10% of an active compound and (B) about 90 to about 99.9% of a carrier comprising a) a diluent and m) a solvent. Preferably, component a) is propylene glycol and m) is selected from the group consisting of ethanol, ethyl oleate, water, isotonic saline, and combinations thereof.

Compositions for oral administration can have various dosage forms. For example, solid forms include tablets, capsules, granules, and bulk powders. These oral dosage forms comprise a safe and effective amount, usually at least about 1%, and preferably from about 5% to about 50%, of component (A). The oral dosage compositions further comprise (B) about 50 to about 99% of a carrier, preferably about 50 to about 95%.

Tablets can be compressed, tablet triturates, enteric-coated, sugar-coated, film-coated, or multiple-compressed. Tablets typically comprise (A) the active compound, and (B) a carrier comprising ingredients selected from the group consisting of a) diluents, b) lubricants, c) binders, d) disintegrants, e) colorants, f) flavors, g) sweeteners, k) glidants, and combinations thereof. Preferred diluents include calcium carbonate, sodium carbonate, mannitol, lactose, and sucrose. Preferred binders include starch, and gelatin. Preferred disintegrants include alginic acid, and croscarmelose. Preferred lubricants include magnesium stearate, stearic acid, and talc. Preferred colorants are the FD&C dyes, which can be added for appearance. Chewable tablets preferably contain g) sweeteners such as aspartame and saccharin or f) flavors such as menthol, peppermint, and fruit flavors, or both.

Capsules (including time release and sustained release compositions) typically comprise (A) the active compound and (B) the carrier comprising one or more a) diluents disclosed above in a capsule comprising gelatin. Granules typically comprise (A) the active compound, and preferably further comprise k) glidants such as silicon dioxide to improve flow characteristics.

The selection of ingredients in the carrier for oral compositions depends on secondary considerations like taste, cost, and shelf stability, which are not critical for the purposes of this invention. One skilled in the art can optimize appropriate ingredients without undue experimentation.

The solid compositions may also be coated by conventional methods, typically with pH or time-dependent coatings, such that component (A) is released in the gastrointestinal tract at various times to extend the desired action. The coatings typically comprise one or more components selected from the group consisting of cellulose acetate phthalate, polyvinylacetate phthalate, hydroxypropyl methyl cellulose phthalate, ethyl cellulose, acrylic resins such as EUDRAGIT® coatings (available from Rohm & Haas G.M.B.H. of Darmstadt, Germany), waxes, shellac, polyvinylpyrrolidone, and other commercially available film-coating preparations such as Dri-Klear, manufactured by Crompton & Knowles Corp., Mahwah, N.J. or OPADRY® manufactured by Colorcon, Inc., of West Point, Pa.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise (A) the active compound and (B) a carrier comprising ingredients selected from the group consisting of a) diluents, e) colorants, and f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the active compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethylcellulose, and hydroxypropylmethylcellulose. Such compositions may further comprise b) lubricants, e) colorants, f) flavors, g) sweeteners, h) antioxidants, and k) glidants.

The composition may further comprise component (C) one or more optional ingredients. Component (C) can be a therapeutic agent used to treat the underlying disease from which the subject suffers. For example, component (C) can be (i) a cancer therapeutic agent, such as a chemotherapeutic agent or a chemosensitizing agent, or a combination thereof, (ii) an antibacterial agent, (iii) an antiviral agent, (iv) an antifungal agent, and combinations thereof. Component (C) can be coadministered with component (A) to increase the susceptibility of the multidrug resistant cells within the subject to the therapeutic agent.

Suitable (i) cancer therapeutic agents are known in the art. Cancer therapeutic agents include chemotherapeutic agents, chemosensitizing agents, and combinations thereof. Suitable chemotherapeutic agents are disclosed in U.S. Pat. No. 5,416,091, which is hereby incorporated by reference for the purpose of disclosing chemotherapeutic agents. Suitable chemotherapeutic agents include actinomycin D, adriyamycin, amsacrine, colchicine, daunorubicin, docetaxel (which is commercially available as TAXOTERE® from Aventis Pharmaceuticals Products, Inc.), doxorubicin, etoposide, mitoxantrone, mytomycin C, paclitaxel (which is commercially available as TAXOL® from Bristol-Myers Squibb Company of New York, N.Y.), tenipaside, vinblastine, vincristine, and combinations thereof.

Suitable chemosensitizing agents include calcium channel blockers, calmodulin antagonists, cyclic peptides, cyclosporins and their analogs, phenothiazines, quinidine, reserpine, steroids, thioxantheres, transflupentixol, trifluoperazine, and combinations thereof. Suitable chemosensitizing agents are disclosed by Amudkar, et. al in "Biochemical, Cellular, and Pharmacological Aspects of the Multidrug Transporter," Annu. Rev. Pharmacol. Toxicol., 39, pp. 361–398 (1999).

Suitable (ii) antibacterial agents, (iii) antiviral agents, and (iv) antifungal agents are known in the art (see "Annual Reports on Medicinal Chemistry—33; Section III Cancer and Infectious Diseases" ed. Plattner, J., Academic Press, Ch. 12, pp. 121–130 (1998)). Suitable antibacterial agents include quinolones, fluoroquinolones, β-lactam antibiotics, aminoglycosides, macrolides, glycopeptides, tetracyclines, and combinations thereof.

Suitable (iii) antiviral agents include protease inhibitors, DNA synthase inhibitors, reverse transcription inhibitors, and combinations thereof.

Suitable (iv) antiflngal agents include azoles, such as ketoconazole, fluconazole, itraconazole, and combinations thereof.

One skilled in the art will recognize that these therapeutic agents are exemplary and not limiting, and that some may be used in the treatment of various multidrug resistant conditions and diseases. One skilled in the art would be able to select therapeutic agents without undue experimentation.

The amount of component (C) used in combination with component (A), whether included in the same composition or separately coadministered, will be less than or equal to that used in a monotherapy. Preferably, the amount of component (C) is less than 80% of the dosage used in a monotherapy. Monotherapeutic dosages of such agents are known in the art.

Component (C) may be part of a single pharmaceutical composition or may be separately administered at a time before, during, or after administration of component (A), or combinations thereof.

In a preferred embodiment, the composition of this invention comprises component (A), component (B), and (C) a chemotherapeutic agent. In an alternative preferred embodiment, the composition comprises component (A), component (B), and (C) a chemosensitizing agent. In another preferred alternative embodiment, the composition comprises component (A), component (B), and (C) both a chemotherapeutic agent and a chemosensitizing agent.

The exact amounts of each component in the systemic compositions depend on various factors. These factors include the specific compound selected as component (A), and the mode by which the composition will be administered. The amount of component (A) in the systemic composition is typically about 1 to about 99%.

The systemic composition preferably further comprises 0 to 99% component (C), and a sufficient amount of component (B) such that the amounts of components (A), (B), and (C), combined equal 100%. The amount of (B) the carrier employed in conjunction with component (A) is sufficient to provide a practical quantity of composition for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Topical Compositions

Topical compositions comprise: component (A), described above, and component (B) a carrier. The carrier of the topical composition preferably aids penetration of component (A) into the skin. Topical compositions preferably further comprise (C) the optional ingredient described above.

Component (B) the carrier may comprise a single ingredient or a combination of two or more ingredients. In the topical compositions, component (B) is a topical carrier. Preferred topical carriers comprise one or more ingredients selected from the group consisting of water, alcohols, aloe vera gel, allantoin, glycerin, vitamin A and E oils, mineral oil, propylene glycol, polypropylene glycol-2 myristyl propionate, dimethyl isosorbide, combinations thereof, and the like. More preferred carriers include propylene glycol, dimethyl isosorbide, and water.

The topical carrier may comprise one or more ingredients selected from the group consisting of q) emollients, r) propellants, s) solvents, t) humectants, u) thickeners, v) powders, and w) fragrances in addition to, or instead of, the preferred topical carrier ingredients listed above. One skilled in the art would be able to optimize carrier ingredients for the topical compositions without undue experimentation.

Ingredient q) is an emollient. The amount of ingredient q) in the topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate, polydimethylsiloxane, and combinations thereof. Preferred emollients include stearyl alcohol and polydimethylsiloxane.

Ingredient r) is a propellant. The amount of ingredient r) in the topical composition is typically about 5 to about 95%. Suitable propellants include propane, butane, isobutane, dimethyl ether, carbon dioxide, nitrous oxide, nitrogen, and combinations thereof.

Ingredient s) is a solvent. The amount of ingredient s) in the topical composition is typically about 5 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Preferred solvents include ethyl alcohol.

Ingredient t) is a humectant. The amount of ingredient t) in the topical composition is typically about 5 to about 95%. Suitable humectants include glycerin, sorbitol, sodium 2-pyrrolidone-5-carboxylate, soluble collagen, dibutyl phthalate, gelatin, and combinations thereof. Preferred humectants include glycerin.

Ingredient u) is a thickener. The amount of ingredient u) in the topical composition is typically 0 to about 95%.

Ingredient v) is a powder. The amount of ingredient v) in the topical composition is typically 0 to about 95%. Suitable powders include chalk, talc, fullers earth, kaolin, starch, gums, colloidal silicon dioxide, sodium polyacrylate, tetraalkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

Ingredient w) is a fragrance. The amount of ingredient w) in the topical composition is typically about 0.001 to about 0.5%, preferably about 0.001 to about 0.1%.

Ingredient x) is a wax. Waxes useful in this invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point between 40 and 100° C. The amount of ingredient x) in the topical composition is typically about 1 to about 99%.

In an alternative embodiment of the invention, the active compounds may also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. A preferred composition for topical delivery of the present compounds uses liposomes as described in Dowton et al., "Influence of Liposomal Composition on Topical Delivery of Encapsulated Cyclosporin A: I. An in vitro Study Using Hairless Mouse Skin", *S. T. P. Pharma Sciences*, Vol. 3, pp. 404–407 (1993); Wallach and Philippot, "New Type of Lipid Vesicle: Novasome®", *Liposome Technology,* Vol. 1, pp. 141–156 (1993); U.S. Pat. Nos. 4,911,928, and 5,834,014.

The exact amounts of each component in the topical composition depend on various factors. Including the specific compound selected for component (A) and the mode by which the composition will be administered. However, the amount of component (A) typically added to the topical composition is about 0.1 to about 99%, preferably about 1 to about 10%.

The topical composition preferably further comprises 0 to about 99% component (C), more preferably 0 to abut 10%, and a sufficient amount of component (B) such that the amounts of components (A), (B), and (C), combined equal 100%. The amount of (B) the carrier employed in conjunction with component (A) is sufficient to provide a practical quantity of composition for administration per unit dose of the compound. Techniques and compositions for making dosage forms useful in the methods of this invention are described in the following references: *Modern Pharmaceutics,* Chapters 9 and 10, Banker & Rhodes, eds. (1979); Lieberman et al., *Pharmaceutical Dosage Forms: Tablets* (1981); and Ansel, *Introduction to Pharmaceutical Dosage Forms,* $2^{nd}$ Ed., (1976).

Topical compositions that can be applied locally to the skin may be in any form including solutions, oils, creams, ointments, gels, lotions, shampoos, leave-on and rinse-out hair conditioners, milks, cleansers, moisturizers, sprays, skin patches, and the like.

Component (A) may be included in kits comprising component (A), a systemic or topical composition described above, or both; and information, instructions, or both that use of the kit will provide treatment for multidrug resistance (particularly in humans). The information and instructions may be in the form of words, pictures, or both, and the like. In addition or in the alternative, the kit may comprise component (A), a composition, or both; and information, instructions, or both, regarding methods of administration of component (A) or the composition, preferably with the benefit of treating multidrug resistance in mammals.

In an alternative embodiment of the invention, components (A) and (C) may be included in kits comprising components (A) and (C), systemic or topical compositions described above, or both; and information, instructions, or both that use of the kit will provide treatment for multidrug resistance (particularly humans). The information and instructions may be in the form of words, pictures, or both, and the like. In addition or in the alternative, the kit may comprise components (A) and (C), compositions, or both; and information, instructions, or both, regarding methods of administration of components (A) and (C) or the compositions, preferably with the benefit of treating multidrug resistance in mammals.

Methods of Use of the Invention

This invention relates to a method of inhibiting a transport protein. The method comprises administering to a mammal in need of treatment, (A) an active compound described above.

This invention further relates to a method for treating multidrug resistance. The method comprises administering to a mammal (preferably a human) suffering from multidrug resistance, (A) an active compound described above. For example, a mammal diagnosed with multidrug resistant cancer can be treated by the methods of this invention. Preferably, a systemic or topical composition comprising (A) the active compound and (B) the carrier is administered to the mammal. More preferably, the composition is a systemic composition comprising (A) the active compound, (B) the carrier, and (C) an optional ingredient such as a therapeutic agent. Component (A) may be administered before, during, or after administration of component (C). A preferred administration schedule is a continuous infusion over the 24 hour period during which component (C) is also administered.

The dosage of component (A) administered depends on various factors, including the method of administration, the physical attributes of the subject (e.g., age, weight, and gender), and the condition from which the subject suffers. Effective dosage levels for treating or preventing MDR range from about 0.01 to about 100 mg/kg body weight per day, preferably about 0.5 to about 50 mg/kg body weight per day of (A) a compound of this invention. These dosage ranges are merely exemplary, and daily administration can be adjusted depending on various factors. The specific dosage of the active compound to be administered, as well as the duration of treatment, and whether the treatment is topical or systemic are interdependent. The dosage and treatment regimen will also depend upon such factors as the specific active compound used, the treatment indication, the efficacy of the active compound, the personal attributes of the subject (such as, for example, weight, age, sex, and medical condition of the subject), compliance with the treatment regimen, and the presence and severity of any side effects of the treatment.

In addition to the benefits in treating multidrug resistance in subjects suffering from cancer, the active compounds in the compositions and methods of this invention can also be used to treat other conditions. These other conditions include other types of multidrug resistance (i.e., in addition to cancer multidrug resistance) such as bacterial, viral, and fungal multidrug resistance. For example, many of the FDA approved HIV protease inhibitors used to treat AIDS patients suffering from the HIV virus are substrates for Pgp. Therefore, in an alternative embodiment of this invention, an active compound of this invention is coadministered with a therapeutic agent such as an HIV protease inhibitor.

The active compounds and compositions of this invention can also be administered with other therapeutic agents such as oral drugs. The active compounds and compositions can be used to enhance oral drug absorption and increase bioavailability of various drugs.

The active compounds and compositions can also be used to aid drug delivery through the blood-brain barrier for, e.g., enhancing the effectiveness of drugs to treat Alzheimer's disease, treating memory disorders, enhancing memory performance, or treating any other central nervous system disorder where drug delivery is compromised via this transport pump mechanism.

The active compounds and compositions can also be administered to treat subjects suffering from neurological disorders such as spinal injuries, diabetic neuropathy, and macular degeneration.

The active compounds and compositions can also be administered to treat subjects suffering from vision disorders and to improve vision.

The active compounds and compositions can also be administered to treat hair loss. "Treating hair loss" includes arresting hair loss, reversing hair loss, and promoting hair growth.

The active compounds and compositions can also be adminstered to treat inflammatory diseases. Inflammatory diseases include irritable bowel disease, arthritis, and asthma.

EXAMPLES

These examples are intended to illustrate the invention to those skilled in the art and should not be interpreted as limiting the scope of the invention set forth in the claims. The active compounds of this invention can be made using conventional organic syntheses, which are readily available to one skilled in the art without undue experimentation. Such syntheses can be found in standard texts such as J. March, *Advanced Organic Chemistry*, John Wiley & Sons, 1992. One of ordinary skill in the art will appreciate that certain reactions are best carried out when other functionalities are masked or protected in the compound, thus increasing the yield of the reaction or avoiding any undesirable side reactions. The skilled artisan may use protecting groups to accomplish the increased yields or to avoid the undesired reactions. These reactions can be found in the literature, see for example, Greene, T. W. and Wuts, P. G. M., *Protecting Groups in Organic Synthesis*, 2$^{nd}$ ed., John Wiley & Sons, 1991.

The starting materials for preparing the compounds of the invention are known, made by known methods, or commercially available. The starting materials for preparing the compounds of the invention may include the following.

The following reagents are available from Aldrich Chemical Company, Milwaukee, Wis.: 1-bromo-3-phenylpropane, 5-hydroxyquinoline, (R)-(−)-glycidyl tosylate, 3,4-pyridinedicarboxylic acid, 4-phenylbutylamine, 3-pyridinepropionic acid, tert-butyl[S-(R*, R*)]-(−)-(1-oxiranyl)-2-phenylethyl)carbamate, epichlorohydrin, 3,4,5-trimethoxybenzoyl chloride, N,N-diisopropylethylamine, 4-dimethylaminopyridine, 1-hydroxybenzotriazole, 4-trans-aminomethylcyclohexanecarboxylic acid, 3,4,5-trimethoxybenzylamine, and 2,2,4-trimethyl-2-oxazoline.

The following reagents are available from Lancaster Synthesis Inc., Windham, NH: 4-phenylbutyronitrile, 1-tert-butoxycarbonyl-piperidine-3-carboxylic acid, 1-benzyl-4-aminopiperidine, 3,4-dimethoxybenzenesulfonyl chloride, and 1-benzyl-4-homopiperazine.

The following reagents are available from Fluka Chemie AG, Milwaukee, Wis.: 1-tert-butoxycarbonyl-piperidine-4-carboxylic, and (benzotriazol-1-yloxy)tripyrrolidinophosphonium hexafluorophosphate ("PyBOP"), N-(tert-butoxycarbonyl)-iminodiacetic acid, and 1-(diphenylmethyl)piperazine.

The following reagents are available from Acros Organics, Pittsburgh, Pa.: quinoline-6-carboxylic acid and quinoline-5-carboxylic acid.

The following reagent is available from Bachem Bioscience, King of Prussia, Pa.: tert-butoxycarbonyl-β-(3-pyridyl)-alanine.

The following reagent is available from Sigma Chemical Company, Milwaukee, Wis.: N-(3-dimethylaminopropyl)-N'-ethylcarbodiimide hydrochloride.

Various abbreviations are used herein. Abbreviations that can be used and their definitions are shown below in Table 5.

TABLE 5

Abbreviations

| Abbreviation | Definition |
|---|---|
| "AM" | acetoxymethyl ester |
| "Boc" | tert-butoxycarbonyl |

TABLE 5-continued

Abbreviations

| Abbreviation | Definition |
|---|---|
| "CIMS" | chemical ionization mass spectrometry |
| "DMF" | dimethylformamide |
| "ESMS" | electrospray mass spectrometry |
| "Et" | an ethyl group |
| "Me" | a methyl group |
| "MH+" | parent ion in ESMS |
| "MS" | mass spectrometry |
| "MTT" | 3-[4,5-dimethyl-thiazoyl-2-yl]2,5-diphenyl-tetrazolium bromide |
| "NIH" | National Institute of Health |
| "PBS" | Phosphate-buffered saline |
| "THF" | tetrahydrofuran |

Example 1

Preparation of 1,7-diphenyl-4-aminoheptane Hydrochloride (1)

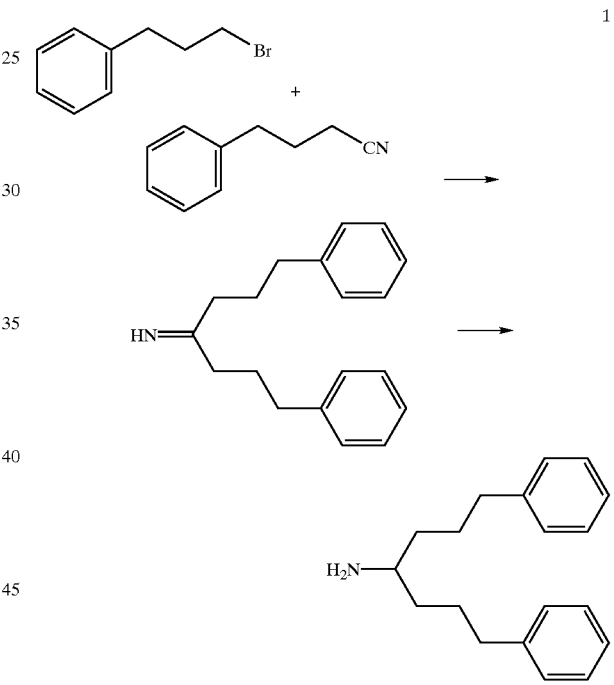

Magnesium (40.2 g, 1.65 mol) and anhydrous ether (3.2 L) are combined in a reaction vessel with stirring. A solution of 1-bromo-3-phenyl propane in 1.6 L of anhydrous ether is added to an addition funnel. The bromide solution is added dropwise to the stirring reaction vessel over a 1 hour period. Upon completion of addition, the mixture stirs for 1–2 hours. A solution of 4-phenylbutyronitrile (160 g, 1.1 mol) in anhydrous ether (2.4 L) is placed in the addition funnel. The solution is added to the reaction vessel over a 1 hour time period. Upon complete addition the solution is heated to reflux for 10 hours, and then stirs at room temperature for six hours. The reaction mixture is diluted with methanol (3.2 L) using an addition funnel. Sodium borohydride (83.4 g, 2.2 mol) is added in portions. Upon complete addition the reaction is stirred at room temperature for six hours. The reaction mixture is quenched by a slow addition of water (3.2 L). The mixture is diluted with ether (3.2 L) and water (1.6 L). The ether layer is separated and the aqueous layer is extracted twice with ether (3.2 L×2). The combined ether extracts are washed once with sodium chloride solution, dried, filtered, and concentrated in vacuo to give the crude product. This product is diluted in ether (1.2 L) and acidified by slow addition of 1M HCl (1.2 L). The mixture stirs for one hour and is concentrated in vacuo. The resulting precipitate is diluted with acetonitrile and is stirred for 16 hours. The desired 1,7-diphenyl-4-aminoheptane hydrochloride is collected by filtration.

Example 2

Preparation of (R)-5-oxiranylmethoxy-quinoline (2)

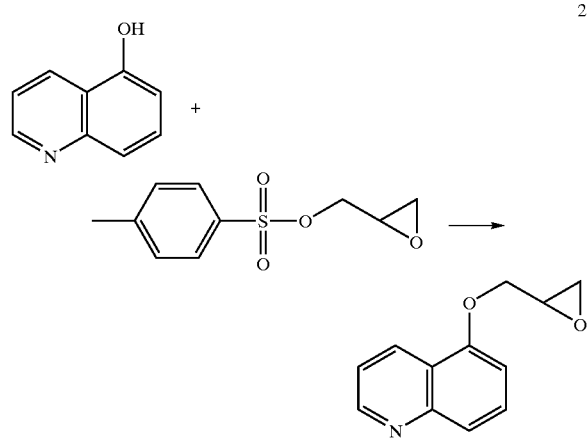

Sodium hydride (60 weight %; 1.79 g; 44.8 mmol) is washed with hexanes (3×10 mL) under an argon blanket. DMF (17 mL) is then added at ambient temperature and the stirred slurry is cooled to 5° C. A solution of 5-hydroxyquinoline (5.00 g; 34.4 mmol) in DMF (65 mL) is added dropwise over 30 minutes. The resulting mixture is allowed to warm to ambient temperature over 1 hour affording a clear, reddish-brown solution. A solution of (R)-(−)-glycidyl tosylate (10.22 g; 44.8 mmol) in DMF (50 mL) is added dropwise over 20 minutes. The resulting mixture is stirred at ambient temperature for 4 hours, quenched by the addition of saturated aqueous ammonium chloride (25 mL), poured onto water (750 mL), and extracted with ether (3×375 mL). The combined ether layers are washed with saturated aqueous sodium bicarbonate (2×375 mL), then dried over MgSO$_4$, filtered, and concentrated in vacuo. The residue is purified via silica gel chromatography with gradient elution (33%→50% ethyl acetate in hexanes) affording the desired product (4.95 g) as a tan solid. ESMS: MH$^+$ 202.2 (base).

Example 3

Preparation of 4-[4-phenyl-1-(3-phenyl-propyl)-butylcarbamoyl]-piperidine-1-carboxylic acid tert-butyl ester (3)

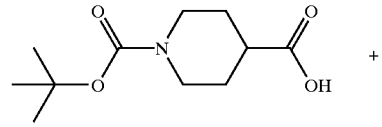

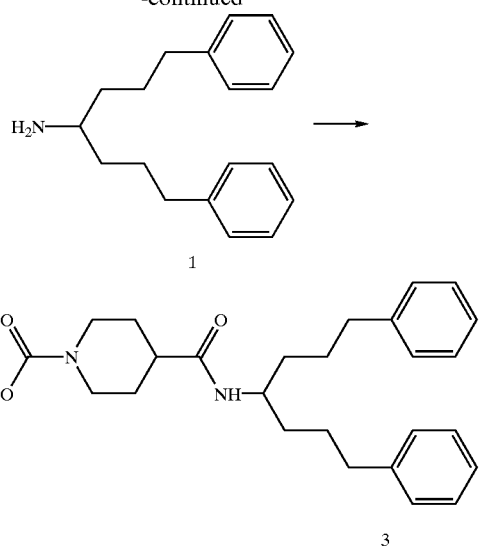

1-tert-Butoxycarbonyl-piperidine-4-carboxylic acid (1 g; 4.36 mmol) is dissolved in methylene chloride (25 mL) at ambient temperature. 1,7-Diphenyl-4-aminoheptane hydrochloride (1) (1.33 g; 4.38 mmol), triethylamine (1.22 mL; 8.75 mmol), and N-(3-dimethylaminopropyl)-N'-ethylcarbodiimide hydrochloride (0.92 g; 4.8 mmol) are added sequentially. The mixture is stirred for 18 hours at ambient temperature then concentrated in vacuo at 40° C. The residue is diluted with ethyl acetate (150 mL) and washed successively with water (150 mL), 0.1 N HCl (100 mL), saturated aqueous sodium bicarbonate (50 mL), and saturated brine (50 mL). The organic layer is dried over MgSO$_4$, filtered, and concentrated in vacuo. The residue is purified via silica gel chromatography with gradient elution (5%→40% ethyl acetate in hexanes) affording the desired product (0.77 g) as a solid.

Example 4

Preparation of Piperidine-4-carboxylic acid [4-phenyl-1-(3-phenyl-propyl)-butyl]-amide (4)

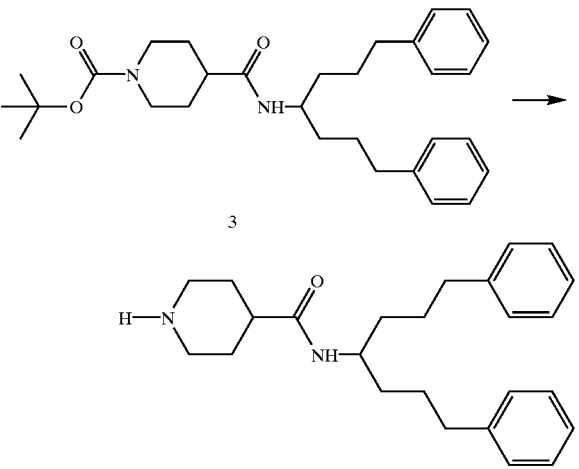

4-[4-Phenyl-1-(3-phenyl-propyl)-butylcarbamoyl]-piperidine-1-carboxylic acid tert-butyl ester (3) (0.77 g; 1.61 mmol) is dissolved in methylene chloride (20 mL) at ambient temperature. Trifluoroacetic acid (20 mL) is added in a slow stream, and the solution is stirred for 90 minutes at ambient temperature. The solution is concentrated in vacuo at 40° C. The residue is slurried in a mixture of methylene chloride (10 mL) and water (100 mL), then potassium carbonate is added until the slurry is alkaline. The slurry is diluted with water (200 mL) then extracted with methylene chloride (3×100 mL). The organic extracts are dried over MgSO₄, filtered, and concentrated in vacuo affording the desired product (0.58 g) as an oil.

Example 5

Preparation of 1-(1-tert-butoxycarbonylpiperidine-2-carbonyl)-piperidine-4-carboxylic acid [4-phenyl-1-(3-phenyl-propyl)-butyl]-amide (5)

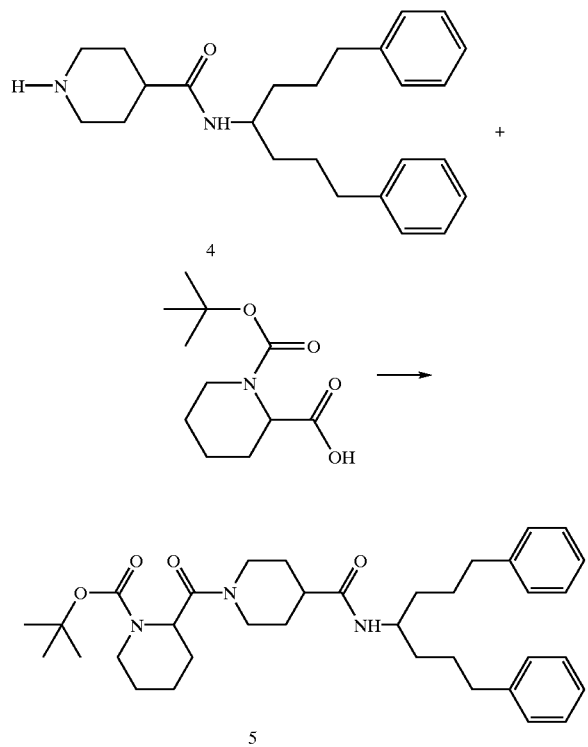

Piperidine-4-carboxylic acid [4-phenyl-1-(3-phenyl-propyl)-butyl]-amide (4) (1.00 g; 2.64 mmol) is dissolved in methylene chloride (25 mL) at ambient temperature. 1-tert-Butoxycarbonyl-piperidine-4-carboxylic acid (0.73 g; 3.17 mmol), N,N-diisopropylethylamine (0.75 g; 5.81 mmol) and PyBOP (1.65 g; 3.17 mmol) are added sequentially. The reaction is stirred for 20 hours at room temperature, then concentrated under reduced pressure. The residue is purified via silica gel chromatography (50%→70% ethyl acetate in hexanes) affording the desired product (5) as a solid. ESMS: MH⁺ 590.6

Example 6

Preparation of 1-(piperidine-2-carbonyl)-piperidine-4-carboxylic acid [4-phenyl-1-(3-phenyl-propyl)-butyl]-amide (6)

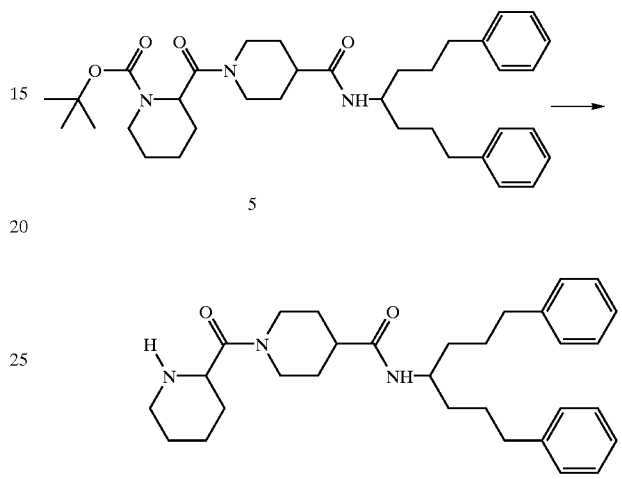

1-(1-tert-Butoxycarbonylpiperidine-2-carbonyl)-piperidine-4-carboxylic acid [4-phenyl-1-(3-phenyl-propyl)-butyl]-amide (5) (1.41 g; 2.39 mmol) is dissolved in methylene chloride (40 mL) at ambient temperature. Trifluoroacetic acid (20 mL) is added in a slow stream, and the solution is stirred for 1.5 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken the layers separated. The water layer is extracted with methylene chloride (3×50 mL). The combined organic extracts are washed with water, dried over MgSO₄, filtered, and concentrated in vacuo affording the desired product (1.10 g) as a white solid. ESMS: MH⁺ 490.2

Example 7

Preparation of N-{1-[2-(R)-hydroxy-3-(quinolin-5-yloxy)-propyl]-piperidine-2-carbonyl}-piperidine-4-carboxylic acid [4-phenyl-1-(3-phenyl-propyl)-butyl]-amide (7)

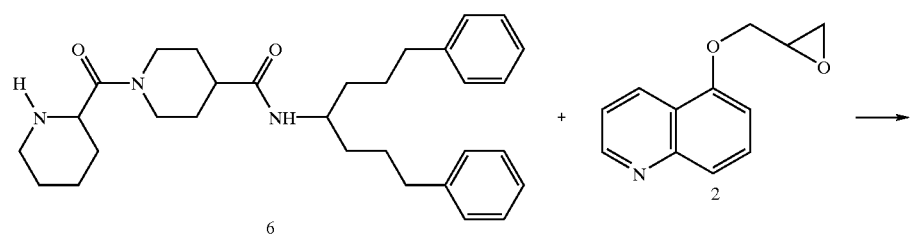

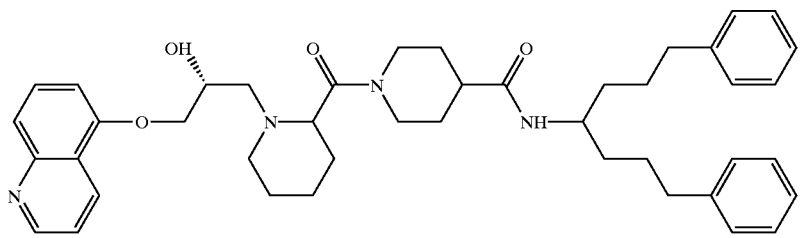

1-(Piperidine-2-carbonyl)-piperidine-4-carboxylic acid [4-phenyl-1-(3-phenyl-propyl)-butyl]-amide (6) (243.4 mg; 0.497 mmol) is dissolved in ethanol (12 mL) at ambient temperature. (R)-5-Oxiranylmethoxy-quinoline (2) (100.0 mg; 0.497 mmol) is added, then the mixture is refluxed for 17 hours. After cooling to ambient temperature, the solution is concentrated in vacuo at 40° C. The residue is purified via silica gel chromatography with gradient elution (50%→100% acetone in hexanes, then 5%→20% ethanol in acetone) affording the desired product (240 mg) as a white solid. ESMS: MH$^+$ 691.4

Example 8

Preparation of N-(3,4-dimethoxybenzenesulfonyl)-[(2S,4R)-4-hydroxy-2-pyrrolidinecarboxylic acid] methyl ester (8)

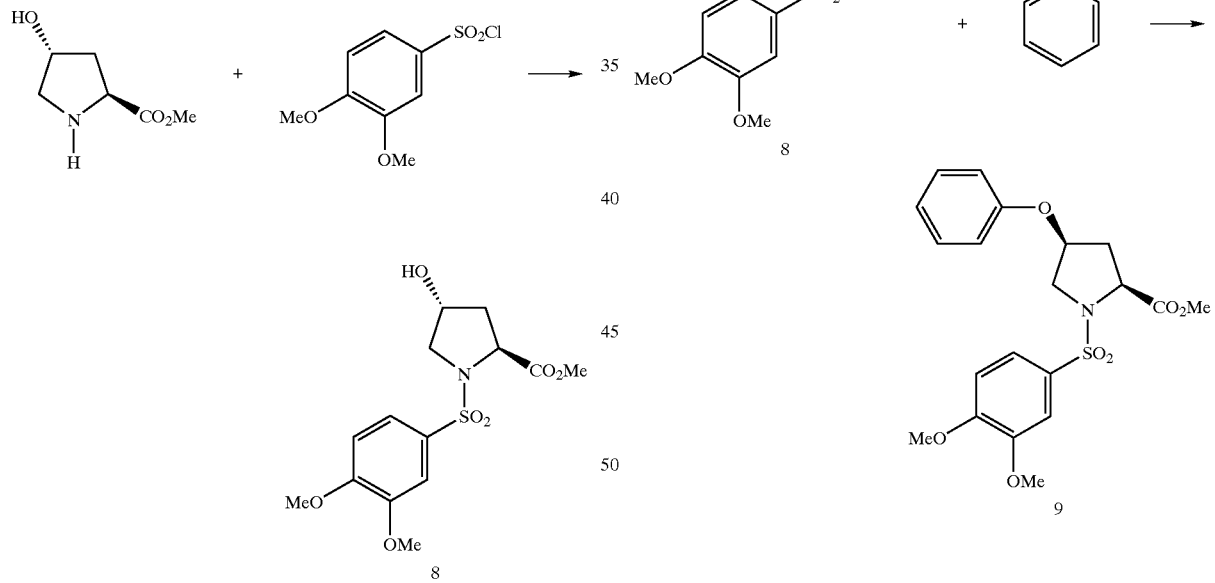

[(2S,4R)-4-hydroxy-2-pyrrolidinecarboxylic acid] methyl ester (3.00 g, 20.7 mmol) is dissoved in methylene chloride (120 mL). Triethylamine (5.23 g, 51.7 mmol) and 4-(dimethylamino)pyridine (0.25 g, 2.1 mmol) are added and the solution is cooled in an ice-bath. 3,4-Dimethoxybenzenesulfonyl chloride (6.36 g, 26.9 mmol) is added. After 15 minutes the cooling bath is removed and the reaction allowed to warm to ambient temperature. After 1 hour the reaction mixture is poured onto ice-cold 0.1N HCl (150 mL) and extracted with methylene chloride (1×150 mL, 2×75 mL). The combined organic extracts are washed with water, dried over MgSO$_4$, filtered, and concentrated in vacuo. The residue is purified via silica gel chromatography (20% ethyl acetate in hexanes) affording the desired product as a solid. CIMS: MH$^+$ 346

Example 9

Preparation of N-(3,4-dimethoxybenzenesulfonyl)-[(2S,4S)-4-phenoxy-2-pyrrolidinecarboxylic acid] methyl ester (9)

N-(3,4-Dimethoxybenzenesulfonyl)-[(2S,4R)-4-hydroxy-2-pyrrolidinecarboxylic acid] methyl ester (8) (1.00 g, 2.90 mmol), phenol (0.41 g, 4.34 mmol) and triphenylphosphine (1.14 g, 4.34) are combined in THF (10 mL). The mixture is cooled in an ice-bath and diethyl azodicarboxylate (0.76 g, 4.34 mmol) is added dropwise over 30 minutes. The reaction is allowed to warm to ambient temperature with overnight stirring. The reaction mixture is concentrated at reduced pressure and treated with ether. The mixture is decanted and the organic extract is concentrated. The residue is purified via silica gel chromatography (40% ethyl acetate in hexanes) affording the desired product as a solid. CIMS: MH$^+$ 422

Example 10

Preparation of N-(3,4-dimethoxybenzenesulfonyl)-[(2S,4S)-4-phenoxy-2-pyrrolidinecarboxylic acid] (10)

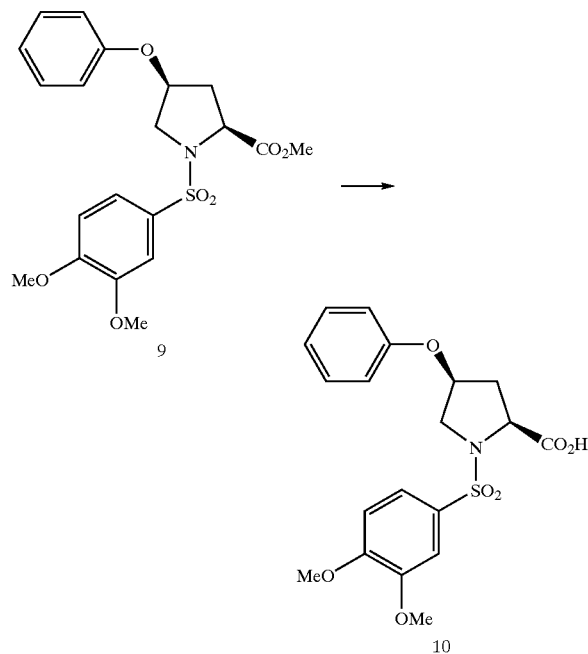

N-(3,4-Dimethoxybenzenesulfonyl)-[(2S,4S)-4-phenoxy-2-pyrrolidinecarboxylic acid] methyl ester (9) (0.95 g, 2.25 mmol) is dissolved in 11 mL of 2:2:1 tetrahydrofuran:water:methanol. Lithium hydroxide (0.54 g, 22.5 mmol) is added and the solution stirred at ambient temperature for 6 hours. The reaction mixture is poured onto saturated citric acid solution (20 mL) and extracted with ethyl acetate (40 mL). The organic layer is isolated and washed successively with water (2×20 mL) and brine (20 mL). The solution is then dried over magnesium sulfate, filtered and concentrated in vacuo to afford the desired product as a white solid. CIMS: MH+ 408

Example 11

Preparation of N-(3,4-dimethoxybenzenesulfonyl)-[(2S,4S)-4-phenoxy-2-pyrrolidinecarboxylic acid] (4-benzhydrylpiperazine-1-yl) amide (11)

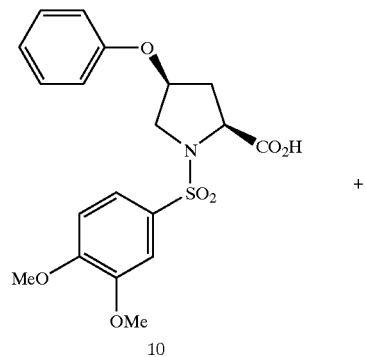

+

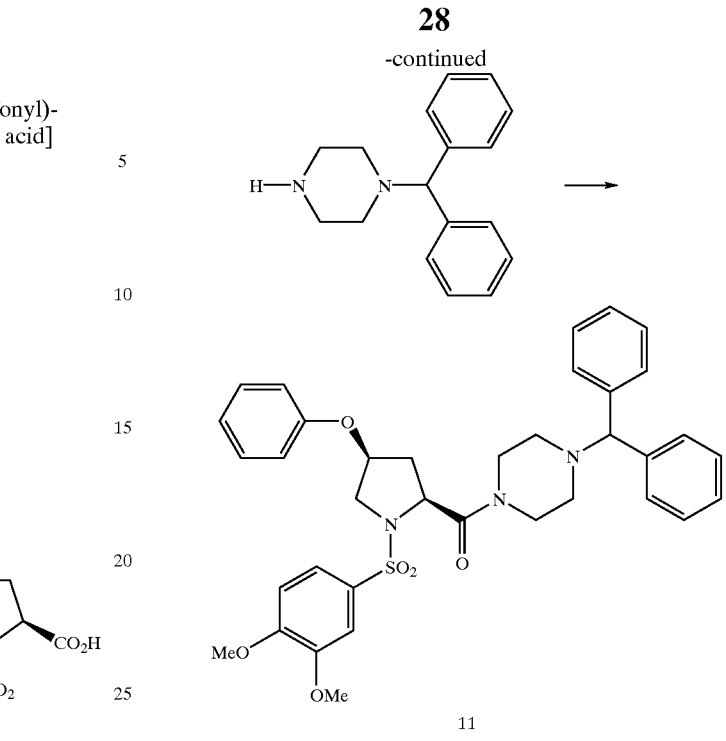

N-(3,4-Dimethoxybenzenesulfonyl)-[(2S,4S)-4-phenoxy-2-pyrrolidinecarboxylic acid] (10) (0.64 g; 1.57 mmol) is dissolved in methylene chloride (15 mL) at ambient temperature. 1-(Diphenylmethyl)piperazine (0.48 g; 1.89 mmol), N,N-diisopropylethylamine (0.45 g; 3.46 mmol) and PyBOP (0.98 g; 1.89 mmol) are added sequentially. The reaction is stirred for 16 hours at room temperature, then concentrated under reduced pressure. The residue is purified via silica gel chromatography (40%→50% ethyl acetate in hexanes) affording the desired product as a solid foam. CIMS: MH+ 642

Example 12

Preparation of 5-phenyl-3-(3,4,5-trimethoxybenzoyl)-oxazolidine-4-carboxylic acid (12)

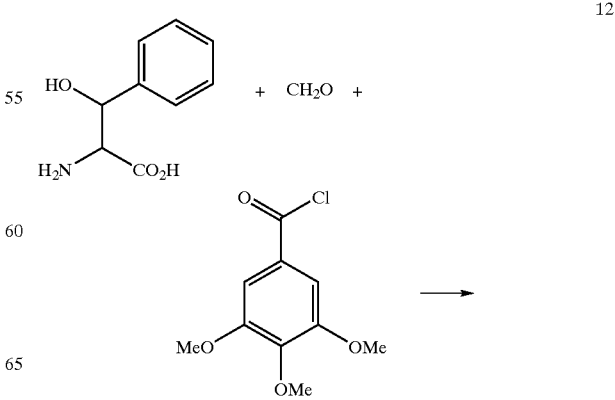

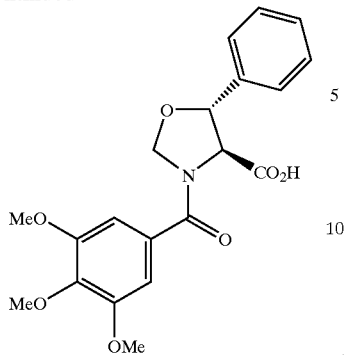

DL-threo-3-Phenylserine hydrate (5.00 g, 27.6 mmol) and 2N NaOH (13.8 mL, 27.6 mmol) are combined and cooled in an ice-bath. Formaldehyde (2.24 g of a 37% aqueous solution) is added and the reaction mixture is stirred at 0° C. for 21 hours. A solution of 3,4,5-trimethoxybenzoyl chloride (6.36 g, 27.6 mmol) in acetone (20 mL) is added slowly using solid sodium bicarbonate to maintain the pH>7. After stirring for 1 hour the reaction mixture is poured onto water and extracted with ethyl acetate (3×50 mL). The aqueous solution is cooled in an ice-bath, the pH is adjusted to 1 with 1N HCl and the mixture is extracted with methylene chloride (3×100 mL). The combined methylene chloride extracts are washed with water, dried over magnesium sulfate, filtered and concentrated at reduced pressure to afford the desired product as a white solid. CIMS: MH$^+$ 388

Example 13

Preparation of 5-phenyl-3-(3,4,5-trimethoxybenzoyl)-oxazolidine-4-carboxylic acid (4-benzhydrylpiperazine-1-yl) amide (13)

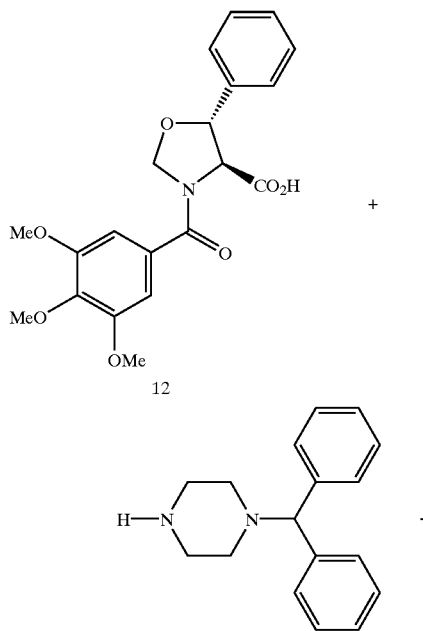

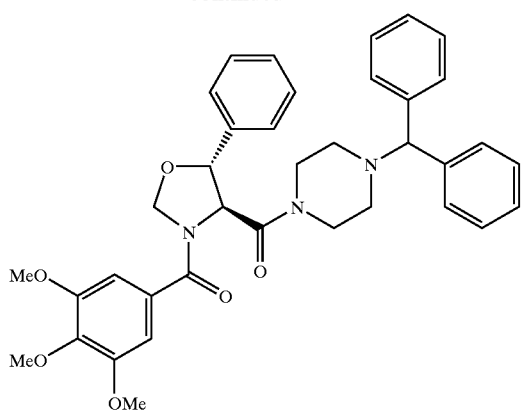

5-Phenyl-3-(3,4,5-trimethoxybenzoyl)-oxazolidine-4-carboxylic acid (12) (120 mg; 0.310 mmol) is dissolved in methylene chloride (3 mL) at ambient temperature. 1-(Diphenylmethyl)piperazine (94 mg; 0.372 mmol), N,N-diisopropylethylamine (128 mg; 0.99 mmol) and PyBOP (193 mg; 0.372 mmol) are added sequentially. The reaction is stirred for 1 hour at room temperature, then concentrated under reduced pressure. The residue is purified via silica gel chromatography (30%→60% ethyl acetate in hexanes) affording the desired product as a white solid. CIMS: MH$^+$ 622

Example 14

Preparation of N-(tert-butoxycarbonyl)-3-phenyl-[(2S)-2pyrrolidinecarboxylic acid] (4-benzhydrylpiperazine-1-yl) amide (15)

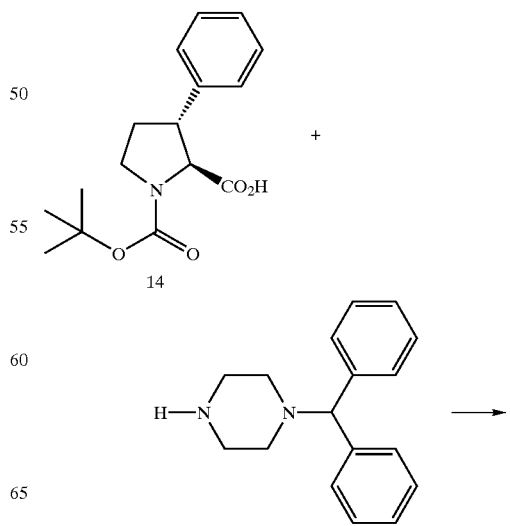

-continued

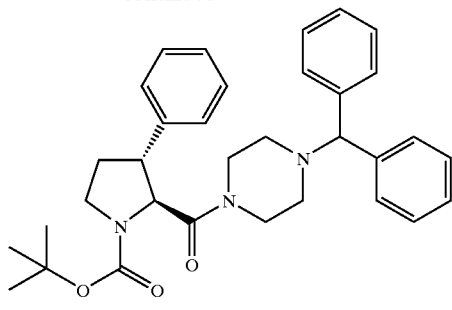

15

N-(tert-Butoxycarbonyl)-3-phenyl-[(2S)-2-pyrrolidinecarboxylic acid] (14) (1.50 g; 5.1 mmol) prepared according to Chung, J. Y. et al., *J. Org Chem.* 55:270–5 (1990) is dissolved in methylene chloride (55 mL) at ambient temperature. 1-(Diphenylmethyl)piperazine (1.62 g; 6.4 mmol), N,N-diisopropylethylamine (1.50 g; 2.25 mmol) and PyBOP (3.35 g; 6.4 mmol) are added sequentially. The reaction is stirred for 18 hours at room temperature, then concentrated under reduced pressure. The residue is purified via silica gel chromatography (33%→50% ethyl acetate in hexanes) affording the desired product as a white solid. CIMS: MH+ 526

Example 15

Preparation of 3-phenyl-[(2S)-2-pyrrolidinecarboxylic Acid] (4-benzhydrylpiperazine-1-yl) amide (16)

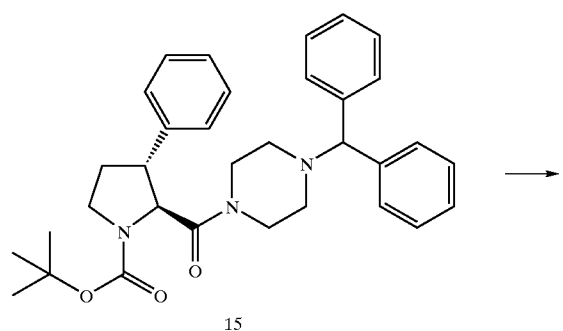

N-(tert-Butoxycarbonyl)-3-phenyl-[(2S)-2-pyrrolidinecarboxylic acid] (4-benzhydrylpiperazine-1-yl) amide (15) (2.70 g; 5.14 mmol) is dissolved in methylene chloride (30 mL) at ambient temperature. Trifluoroacetic acid (20 mL) is added in a slow stream, and the solution is stirred for 2 hours at ambient temperature. The reaction mixture is cooled in an ice-bath and the pH adjusted to 9 with saturated potassium carbonate solution. The mixture is poured onto water (30 mL) and extracted with methylene chloride (1×60 mL, 2×20 mL). The combined organic extracts are washed with water, dried over MgSO$_4$, filtered, and concentrated in vacuo affording the desired product. CIMS: MH+ 426

Example 16

Preparation of 3,4,5-Trimethoxyphenalglyoxylic acid (17)

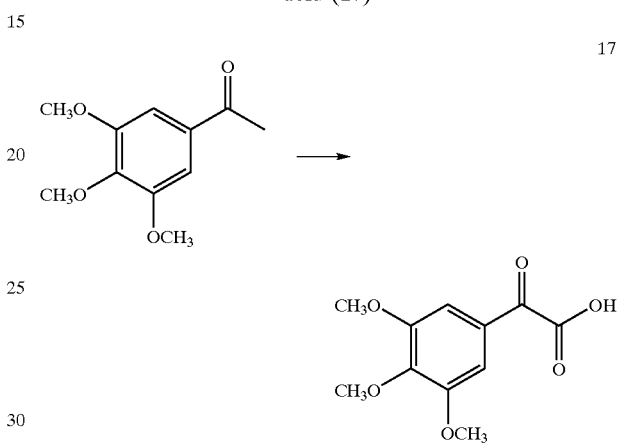

3,4,5-Trimethoxyphenylacetophenone (20.00 g; 0.095 mol) is dissolved in pyridine (76 mL) at ambient temperature. Selenium dioxide (13.8 g; 0.124 mol) is added and the mixture is carefully heated at reflux for 24 hours. The mixture is cooled to ambient temperature then filtered through a pad of diatomaceous earth. The filtrate is concentrated in vacuo at 40° C. The residue is dissolved in ethyl acetate (250 mL) then extracted sequentially with 1N HCl (250 mL), and saturated aqueous sodium bicarbonate (2×100 mL). The combined aqueous bicarbonate extracts are acidified with concentrated HCl, then extracted with ether (2×250 mL). The ether extracts are combined then washed with brine, dried over MgSO$_4$, filtered, and concentrated in vacuo at 40° C. affording the desired product (12.00 g) as a yellow solid.

Example 17

Preparation of N-[3,4,5-trimethoxyphenyl)glyoxylyl]-3-phenyl-[(2S)-2-pyrrolidinecarboxylic acid] (4-benzhydrylpiperazine-1-yl) amide (18)

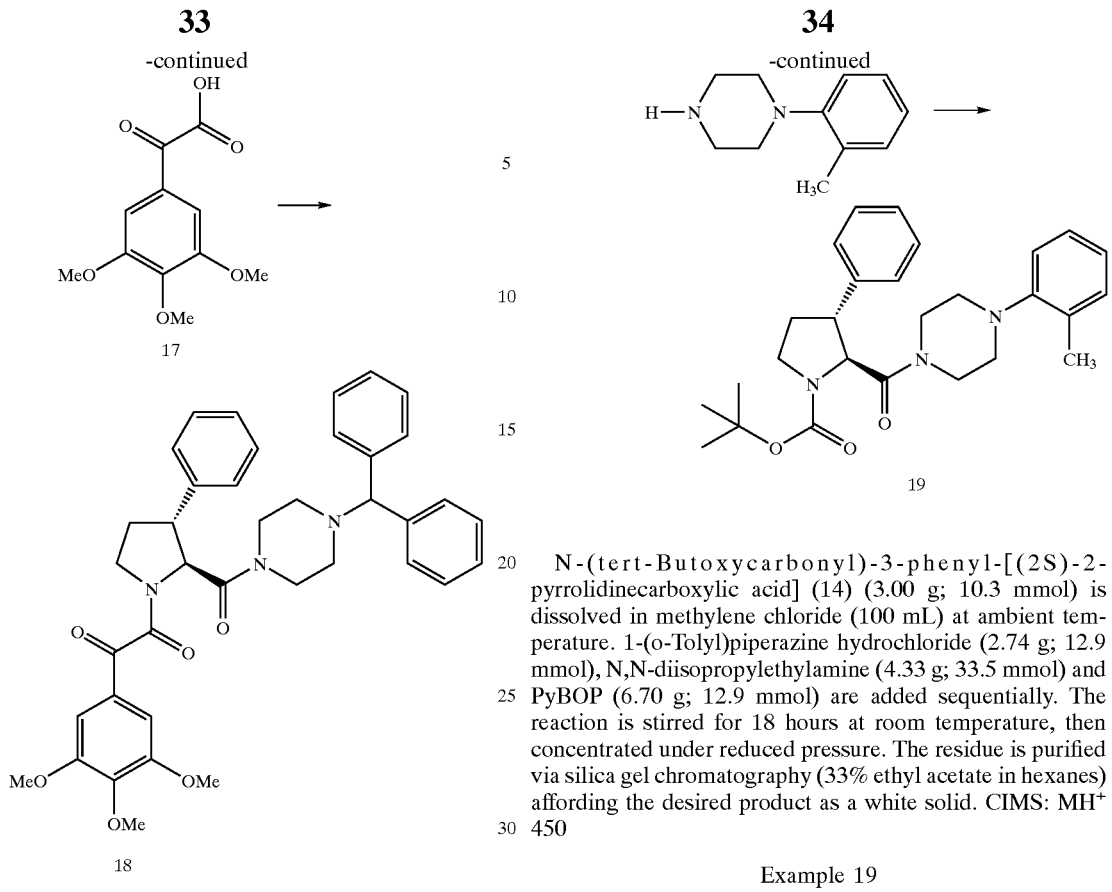

3-Phenyl-[(2S)-2-pyrrolidinecarboxylic acid] (4-benzhydrylpiperazine-1-yl) amide (16) (0.50 g; 1.2 mmol) is dissolved in methylene chloride (15 mL) at ambient temperature. 3,4,5-Trimethoxyphenylglyoxylic acid (17) (0.34 g; 1.40 mmol), N,N-diisopropylethylamine (0.33 g; 2.60 mmol) and PyBOP (0.73 g; 1.40 mmol) are added sequentially. The reaction is stirred for 16.5 hours at room temperature, then concentrated under reduced pressure. The residue is purified via silica gel chromatography (33%→50% ethyl acetate in hexanes) affording the desired product as a solid. CIMS: MH$^+$ 648

Example 18

Preparation of N-(tert-butoxycarbonyl)-3-phenyl-[(2S)-2-pyrrolidinecarboxylic acid] 1-[(o-tolyl)piperazine-1-yl] amide (19)

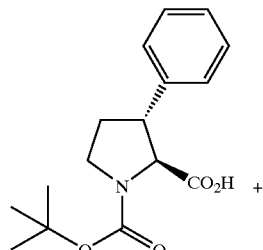

N-(tert-Butoxycarbonyl)-3-phenyl-[(2S)-2-pyrrolidinecarboxylic acid] (14) (3.00 g; 10.3 mmol) is dissolved in methylene chloride (100 mL) at ambient temperature. 1-(o-Tolyl)piperazine hydrochloride (2.74 g; 12.9 mmol), N,N-diisopropylethylamine (4.33 g; 33.5 mmol) and PyBOP (6.70 g; 12.9 mmol) are added sequentially. The reaction is stirred for 18 hours at room temperature, then concentrated under reduced pressure. The residue is purified via silica gel chromatography (33% ethyl acetate in hexanes) affording the desired product as a white solid. CIMS: MH$^+$ 450

Example 19

Preparation of 3-phenyl-[(2S)-2-pyrrolidinecarboxylic acid] 1-[(o-tolyl)piperazine-1-yl)] amide (20)

N-(tert-Butoxycarbonyl)-3-phenyl-[(2S)-2-pyrrolidinecarboxylic acid] [(o-tolyl)piperazine-1-yl) amide (19) (4.46 g; 9.92 mmol) is dissolved in methylene chloride (60 mL) at ambient temperature. Trifluoroacetic acid (40 mL) is added in a slow stream, and the solution is stirred for 1 hour at ambient temperature. The reaction mixture is cooled in an ice-bath and the pH adjusted to 9 with saturated potassium carbonate solution. The mixture is poured onto water (60 mL) and extracted with methylene chloride (1×120 mL, 2×40 mL). The combined organic extracts are washed with water, dried over MgSO$_4$, filtered, and concentrated in vacuo affording the desired product. CIMS: MH$^+$ 350

Example 20

Preparation of N-[(3,4,5-trimethoxyphenyl) glyoxylyl]-3-phenyl-[(2S)-2-pyrrolidinecarboxylic acid] 1-[(o-tolyl)piperazine-1-yl)] amide (21)

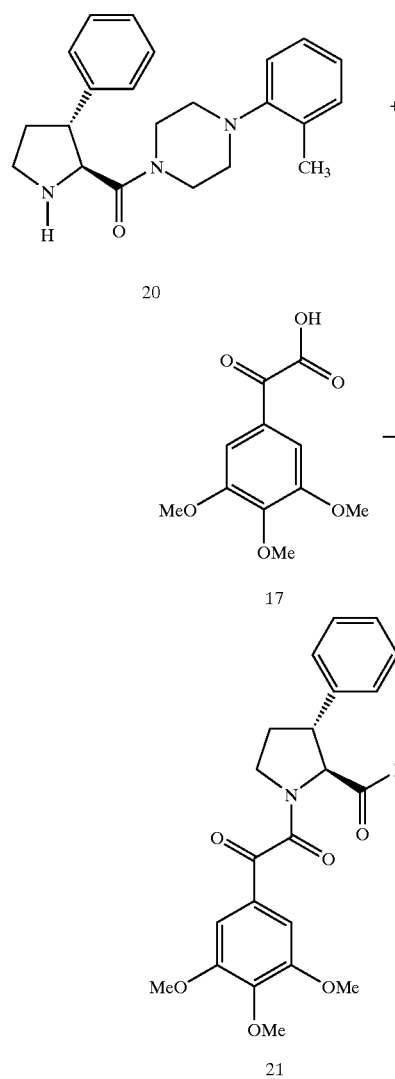

3-Phenyl-[(2S)-2-pyrrolidinecarboxylic acid] [(o-(tolyl) piperazine-1-yl] amide (20) (1.00 g; 2.86 mmol) is dissolved in methylene chloride (40 mL) at ambient temperature. 3,4,5-Trimethoxyphenylglyoxylic acid (17) (0.82 g; 3.43 mmol), N,N-diisopropylethylamine (0.81 g; 6.30 mmol) and PyBOP (1.79 g; 3.43 mmol) are added sequentially. The reaction is stirred for 17.5 hours at room temperature, then concentrated under reduced pressure. The residue is purified via silica gel chromatography (33%→40% ethyl acetate in hexanes) affording the desired product as a solid. CIMS: MH$^+$ 572

Example 21

Preparation of N-(tert-butoxycarbonyl)-3-phenyl-[(2S)-2-pyrrolidinecarboxylic acid] 1-[(2-pyridyl) piperazine-1-yl)] amide (22)

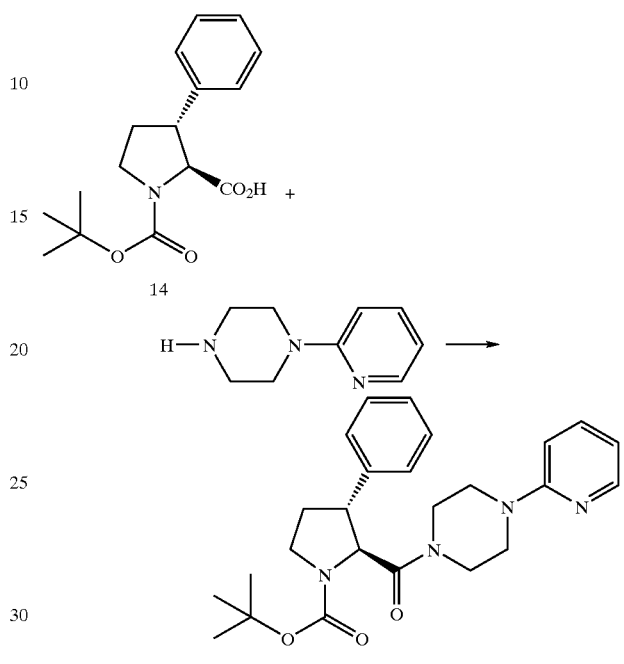

N-(tert-Butoxycarbonyl)-3-phenyl-[(2S)-2-pyrrolidinecarboxylic acid] (14) (1.00 g; 3.43 mmol) is dissolved in methylene chloride (40 mL) at ambient temperature. 1-(2-Pyridyl)piperazine (0.70 g; 4.29 mmol), N,N-diisopropylethylamine (1.00 g; 7.70 mmol) and PyBOP (2.23 g; 4.29 mmol) are added sequentially. The reaction is stirred for 19 hours at room temperature, then concentrated under reduced pressure. The residue is purified via silica gel chromatography (50%→70% ethyl acetate in hexanes) affording the desired product as a white solid. CIMS: MH$^+$ 437

Example 22

Preparation of 3-phenyl-[(2S)-2-pyrrolidinecarboxylic acid] 1-[(2-pyridyl) piperazine-1-yl)] amide (23)

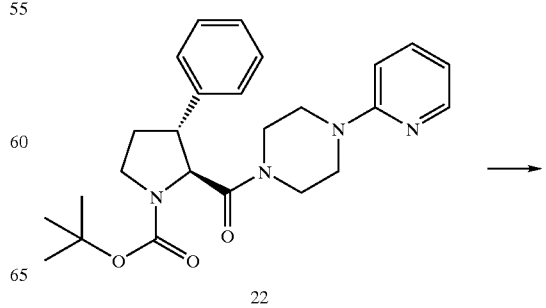

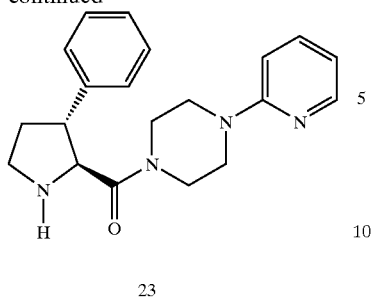

23

N-(tert-Butoxycarbonyl)-3-phenyl-[(2S)-2-pyrrolidinecarboxylic acid] [(2-pyridyl)piperazine-1-yl] amide (22) (1.12 g; 2.57 mmol) is dissolved in methylene chloride (60 mL) at ambient temperature. Trifluoroacetic acid (35 mL) is added in a slow stream, and the solution is stirred for 1 hour at ambient temperature. The reaction mixture is cooled in an ice-bath and the pH adjusted to 9 with saturated potassium carbonate solution. The mixture is poured onto water (60 mL) and extracted with methylene chloride (1×120 mL, 2×40 mL). The combined organic extracts are washed with water, dried over MgSO$_4$, filtered, and concentrated in vacuo affording the desired product. CIMS: MH$^+$ 337

Example 23

Preparation of N-[(3,4,5-trimethoxyphenyl)glyoxylyl]-3-phenyl-[(2S)-2-pyrrolidinecarboxylic acid] 1-[(2-pyridyl)piperazine-1-yl)] amide (24)

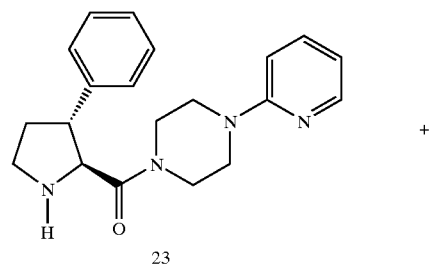

23

+

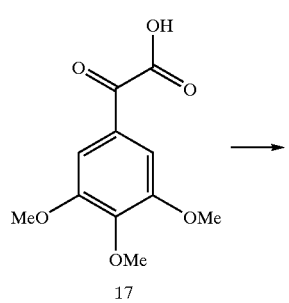

17

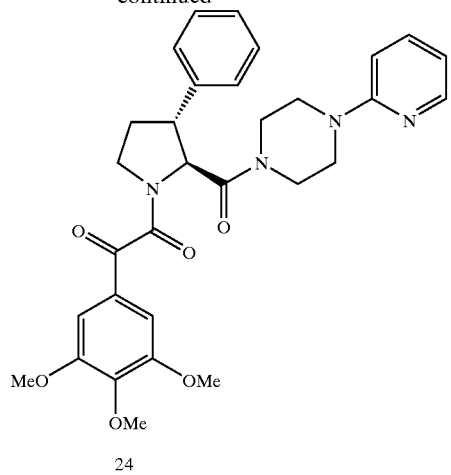

24

3-Phenyl-[(2S)-2-pyrrolidinecarboxylic acid] [(2-pyridyl)piperazine-1-yl] amide (23) (0.97 g; 2.86 mmol) is dissolved in methylene chloride (40 mL) at ambient temperature. 3,4,5-Trimethoxyphenylglyoxylic acid (17) (0.83 g; 3.46 mmol), N,N-diisopropylethylamine (0.82 g; 6.34 mmol) and PyBOP (1.80 g; 3.46 mmol) are added sequentially. The reaction is stirred for 19 hours at room temperature, then concentrated under reduced pressure. The residue is purified via silica gel chromatography (50%→70% ethyl acetate in hexanes) affording the desired product as a solid. CIMS: MH$^+$ 559

Example 24

Preparation of 1-(tert-butoxycarbonyl)-piperidine-3-carboxylic acid [4-phenyl-1-(3-phenyl-propyl)-butyl]-amide (25)

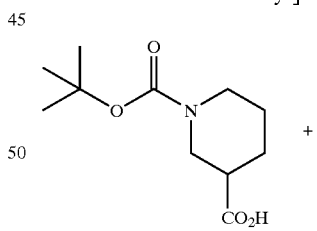

+

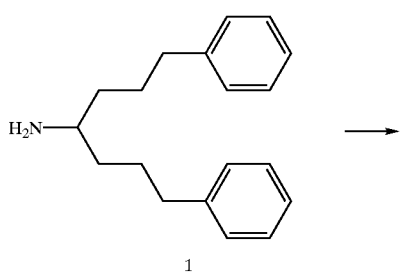

1

-continued

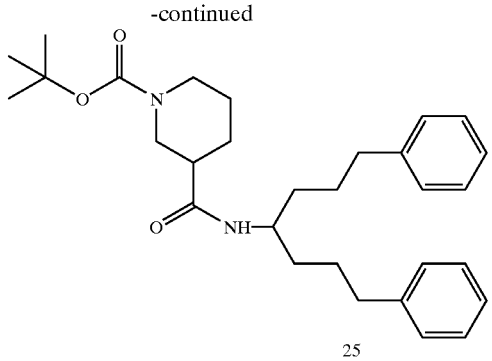

25

1-(tert-Butoxycarbonyl)-piperidine-3-carboxylic acid (3.00 g; 13.1 mmol) is dissolved in methylene chloride (100 mL) at ambient temperature. 1,7-Diphenyl-4-aminoheptane hydrochloride (1) (4.77 g; 15.7 mmol), diisopropylethylamine (7.3 mL; 41.9 mmol), and PyBOP (8.17 g; 15.7 mmol) are added sequentially. The mixture is stirred for 15 hours at ambient temperature then concentrated in vacuo at 40° C. The residue is purified via silica gel chromatography with gradient elution (20%→40% ethyl acetate in hexanes) affording the desired product as an oil. ESMS: MH+ 479.4

Example 25

Preparation of piperidine-3-carboxylic acid [4-phenyl-1-(3-phenyl-propyl)-butyl]-amide (26)

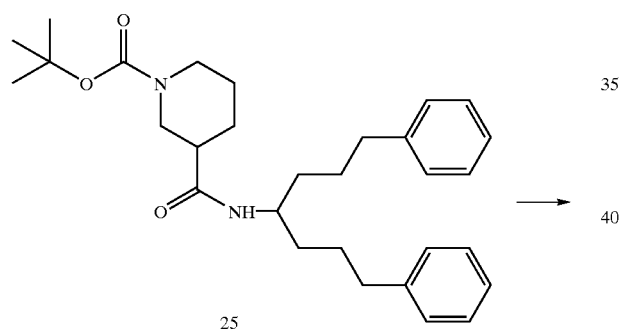

1-(tert-Butoxycarbonyl)-piperidine-3-carboxylic acid [4-phenyl-1-(3-phenyl-propyl)-butyl]-amide (25) (6.30 g; 13.2 mmol) is dissolved in methylene chloride (60 mL) at ambient temperature. Trifluoroacetic acid (40 mL) is added in a slow stream, and the solution is stirred for 1.25 hours at ambient temperature. The solution is concentrated in vacuo at 40° C. The residue is dissolved in methylene chloride (300 mL) and poured onto saturated sodium bicarbonate solution. The pH is adjusted to 9 with saturated potassium carbonate solution. The mixture is shaken and the layers separated. The water layer is extracted with methylene chloride (3×100 mL). The combined organic extracts are washed with water, dried over MgSO₄, filtered, and concentrated in vacuo affording the desired product as a solid. ESMS: MH+ 379.0

Example 26

Preparation of 1-[1-(tert-butoxycarbonyl)piperidine-2-carbonyl]-piperidine-3-carboxylic acid [4-phenyl-1-(3-phenyl-propyl)-butyl]-amide (27)

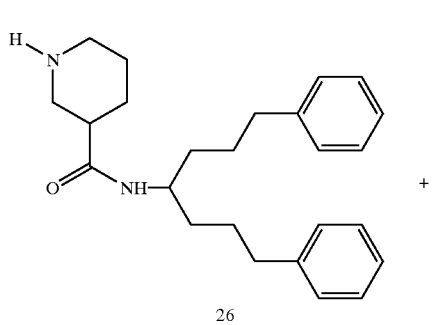

26

+

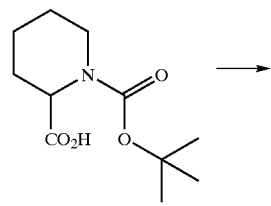

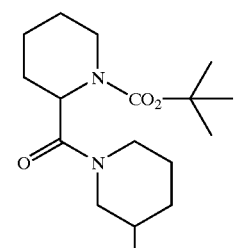

27

Piperidine-3-carboxylic acid [4-phenyl-1-(3-phenyl-propyl)-butyl]-amide (26) (1.00 g; 2.64 mmol) is dissolved in methylene chloride (25 mL) at ambient temperature. 1-tert-Butoxycarbonyl-piperidine-2-carboxylic acid (0.73 g; 3.17 mmol), N,N-diisopropylethylamine (0.75 g; 5.81 mmol) and PyBOP (1.65 g; 3.17 mmol) are added sequentially. The reaction is stirred for 17.5 hours at room temperature, then concentrated under reduced pressure. The residue is purified via silica gel chromatography (40%→60% ethyl acetate in hexanes) affording the desired product (76) as a solid. ESMS: MH+ 590.6

Example 27

Preparation of 1-(piperidine-2-carbonyl)-piperidine-3-carboxylic acid [4-phenyl-1-(3-phenyl-propyl)-butyl]-amide (28)

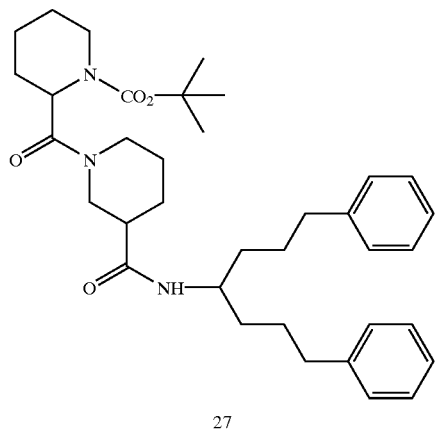

27

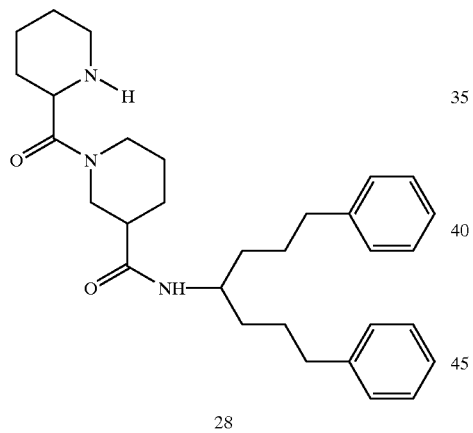

28

1-[1-(tert-Butoxycarbonyl)piperidine-2-carbonyl]-piperidine-3-carboxylic acid [4-phenyl-1-(3-phenyl-propyl)-butyl]-amide (27) (1.35 g; 2.29 mmol) is dissolved in methylene chloride (40 mL) at ambient temperature. Trifluoroacetic acid (20 mL) is added in a slow stream, and the solution is stirred for 4 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken and the layers separated. The water layer is extracted with methylene chloride (3×50 mL). The combined organic extracts are washed with water, dried over MgSO$_4$, filtered, and concentrated in vacuo affording the desired product as a solid foam.

Example 28

Preparation of 1-{1-[2-(R)-hydroxy-3-(quinolin-5-yloxy)-propyl]-piperidine-2-carbonyl}-piperidine-3-carboxylic acid [4-phenyl-1-(3-phenyl-propyl)-butyl]-amide (29)

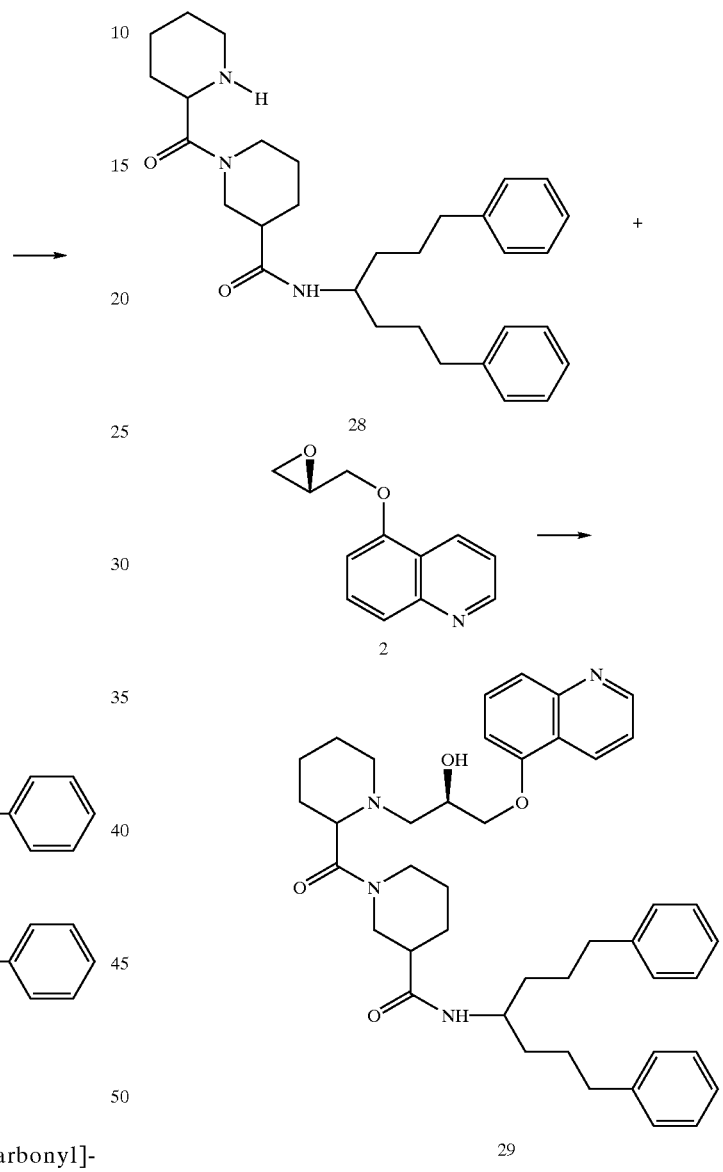

1-(Piperidine-2-carbonyl)-piperidine-3-carboxylic acid [4-phenyl-1-(3-phenyl-propyl)-butyl]-amide (28) (234.4 mg; 0.497 mmol) is dissolved in ethanol (12 mL) at ambient temperature. (R)-5-Oxiranylmethoxy-quinoline (2) (100.0 mg; 0.497 mmol) is added, then the mixture is refluxed for 15 hours. After cooling to ambient temperature, the solution is concentrated in vacuo at 40° C. The residue is purified via silica gel chromatography with gradient elution (90% ethyl acetate in hexanes, 50%→100% acetone in hexanes, then 5% ethanol in acetone) affording the desired product (250 mg) as a white solid. ESMS: MH$^+$691.4

Example 29

Preparation of 1-(tert-butoxycarbonyl)-piperidine-2-carboxylic acid [4-phenyl-1-(3-phenyl-propyl)-butyl]-amide (30)

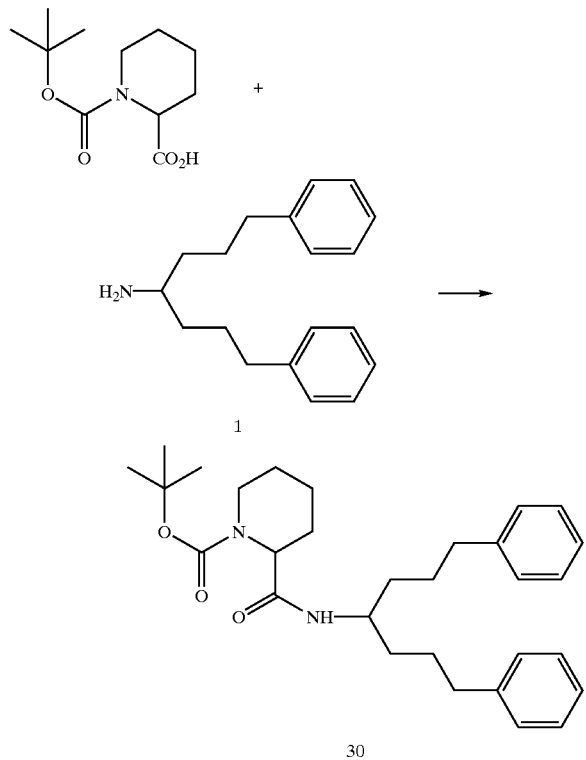

1-(tert-Butoxycarbonyl)-piperidine-2-carboxylic acid (3.00 g; 13.1 mmol) is dissolved in methylene chloride (100 mL) at ambient temperature. 1,7-Diphenyl-4-aminoheptane hydrochloride (1) (4.77 g; 15.7 mmol), diisopropylethylamine (7.3 mL; 41.9 mmol), and PyBOP (8.17 g; 15.7 mmol) are added sequentially. The mixture is stirred for 15 hours at ambient temperature then concentrated in vacuo at 40° C. The residue is purified via silica gel chromatography with gradient elution (10%→30% ethyl acetate in hexanes) affording the desired product as an oil. ESMS: MH$^+$ 479.4

Example 30

Preparation of Piperidine-2-carboxylic acid [4-phenyl-1-(3-phenyl-propyl)-butyl]-amide (31)

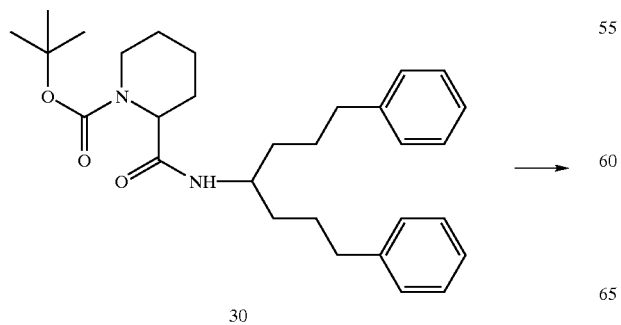

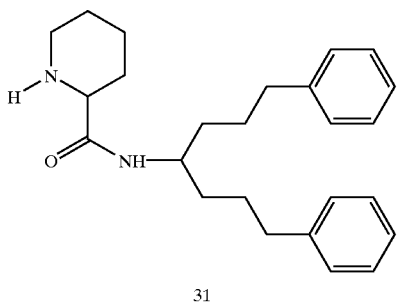

1-(tert-Butoxycarbonyl)-piperidine-2-carboxylic acid [4-phenyl-1-(3-phenyl-propyl)-butyl]-amide (30) (6.77 g; 14.1 mmol) is dissolved in methylene chloride (60 mL) at ambient temperature. Trifluoroacetic acid (40 mL) is added in a slow stream, and the solution is stirred for 1.25 hours at ambient temperature. The solution is concentrated in vacuo at 40° C. The residue is dissolved in methylene chloride (300 mL) and poured onto saturated sodium bicarbonate solution. The pH is adjusted to 9 with saturated potassium carbonate solution. The mixture is shaken and the layers separated. The water layer is extracted with methylene chloride (3×100 mL). The combined organic extracts are washed with water, dried over MgSO$_4$, filtered, and concentrated in vacuo affording the desired product as a solid. ESMS: MH$^+$ 379.2

Example 31

Preparation of 1-[1-(tert-butoxycarbonyl)piperidine-2-carbonyl]-piperidine-2-carboxylic acid [4-phenyl-1-(3-phenyl-propyl)-butyl]-amide (32)

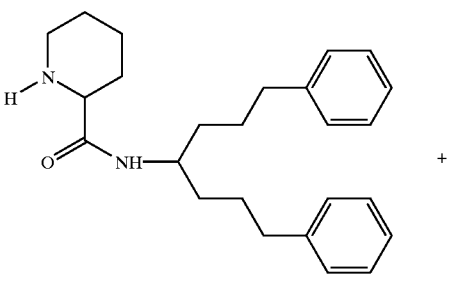

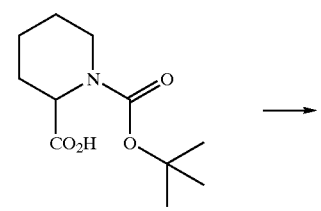

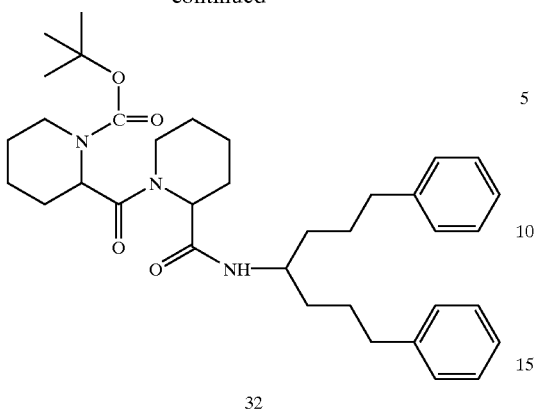

32

Piperidine-2-carboxylic acid [4-phenyl-1-(3-phenyl-propyl)-butyl]-amide (31) (1.00 g; 2.64 mmol) is dissolved in methylene chloride (25 mL) at ambient temperature. 1-tert-Butoxycarbonyl-piperidine-2-carboxylic acid (0.73 g; 3.17 mmol), N,N-diisopropylethylamine (0.75 g; 5.81 mmol) and PyBOP (1.65 g; 3.17 mmol) are added sequentially. The reaction is stirred for 18.5 hours at room temperature, then concentrated under reduced pressure. The residue is purified via silica gel chromatography (20%→40% ethyl acetate in hexanes) affording the desired product (32) as an oil. ESMS: MH+ 590.6

Example 32

Preparation of 1-(piperidine-2-carbonyl)-piperidine-2-carboxylic acid [4-phenyl-1-(3-phenyl-propyl)-butyl]-amide (33)

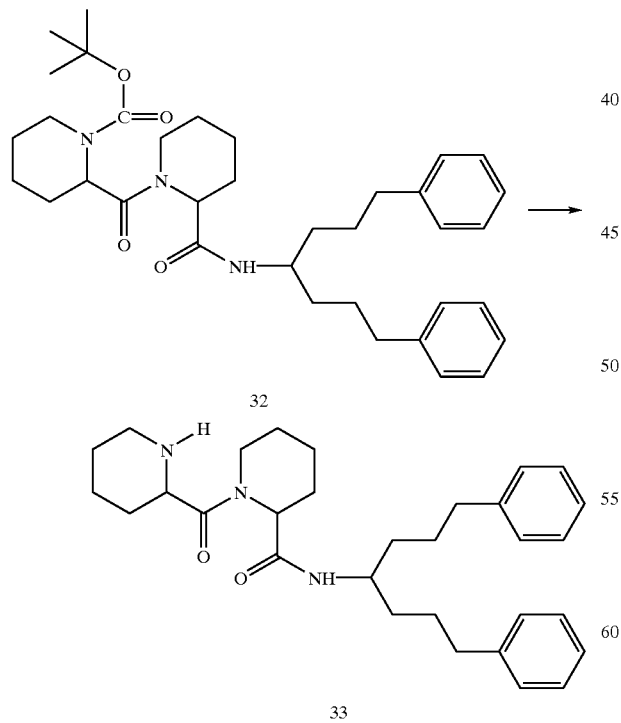

33

1-[1-(tert-Butoxycarbonyl)piperidine-2-carbonyl]-piperidine-2-carboxylic acid [4-phenyl-1-(3-phenyl-propyl)-butyl]-amide (32) (1.05 g; 1.78 mmol) is dissolved in methylene chloride (40 mL) at ambient temperature. Trifluoroacetic acid (20 mL) is added in a slow stream, and the solution is stirred for 4 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken and the layers separated. The water layer is extracted with methylene chloride (3×50 mL). The combined organic extracts are washed with water, dried over MgSO4, filtered, and concentrated in vacuo affording the desired product as an oil.

Example 33

Preparation of 1-{1-[2-(R)-hydroxy-3-(quinolin-5-yloxy)-propyl]-piperidine-2-carbonyl}-piperidine-2-carboxylic acid [4-phenyl-1-(3-phenyl-propyl)-butyl]-amide (34)

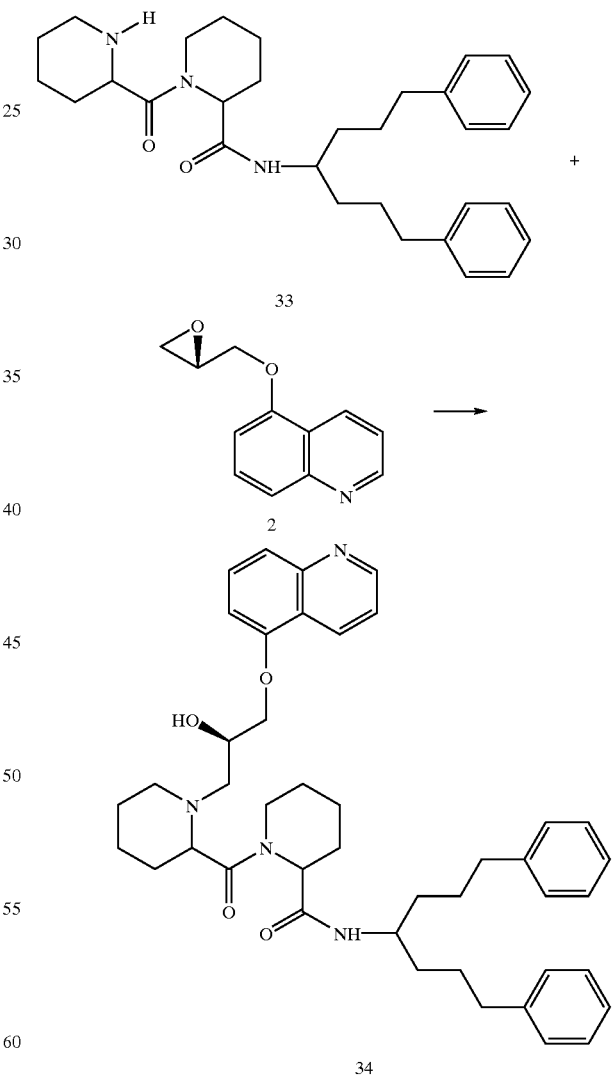

34

1-(Piperidine-2-carbonyl)-piperidine-3-carboxylic acid [4-phenyl-1-(3-phenyl-propyl)-butyl]-amide (33) (234.4 mg; 0.497 mmol) is dissolved in ethanol (12 mL) at ambient temperature. (R)-5-Oxiranylmethoxy-quinoline (2) (100.0 mg; 0.497 mmol) is added, then the mixture is refluxed for 24.5 hours. After cooling to ambient temperature, the solution is concentrated in vacuo at 40° C. The residue is purified via silica gel chromatography with gradient elution (80%→90% ethyl acetate in hexanes, 50%→100% acetone in hexanes, then 5% ethanol in acetone) affording the desired product (250 mg) as a white solid. ESMS: MH+ 691.2

Reference Example 1

Method for Measuring Activity to Inhibit Pgp (Reversal Assay)

NIH-MDR1-G185 cells (obtained from M. Gottesman, NIH) were harvested and resuspended at 6×104 cells/ml in RPMI 1640 containing L-glutamine, 10% Cosmic calf serum, and penicillin-streptomycin. Cell suspension aliquots of 100 microliters were added to individual wells of a 96 well microtiter plate and incubated overnight at 37° C. to allow cells to adhere. Cell viability in the presence of an anticancer drug was determined in the presence and absence of an MDR modifying agent using an MTT assay (P. A. Nelson, et. al, *J. Immunol*, 150:2139–2147 (1993)).

Briefly, cells were preincubated with an MDR modulating agent (final concentration 5 micromolar) for 15 min at 37° C., then treated with varying concentrations of an anticancer agent for 72 hr at 37° C. MTT dye (20 microliters of 5 mg/ml PBS solution) was added to each well and incubated for 4 hr at 37° C. Media was carefully removed and dye was solubilized with 100 microliters of acidified isopropyl alcohol. Absorption was measured on a spectrophotometric plate reader at 570 nm and corrected for background by subtraction at 630 nm. Reversal index was calculated for each MDR modulator and normalized to the reversal index of a benchmark modulator, VX-710 as below:

Reversal index=$IC_{50}$ in the absence of modulator/$IC_{50}$ in the presence of modulator Normalized reversal index=Reversal index of modulator/Reversal index of VX-710

VX-710 is (S)-N-[2-Oxo-2-(3,4,5-trimethoxyphenyl)acetyl] piperidine-2-carboxylic acid 1,7-bis(3-pyridyl)-4-heptyl ester.

Reference Example 2

Method for Measuring Activity to Inhibit Pgp and MRP1 (Calcein AM Extrusion Assay)

Pgp-dependent calcein AM extrusion was measured in NIH-MDR1-G185 cells or HL60-MDR1 cells. MRP1-dependent calcein AM extrusion was measured in HL60/ADR cells. Dye uptake was measured by incubating 0.5–1× 106 cells/ml in cell culture medium containing 0.25 mM calcein AM at 37° C. at an excitation wavelength=493 nm and an emission wavelength=515 nm. Inhibition of calcein AM transport by varying concentrations of MDR modulators was determined by measuring the rate of increase in fluorescence of free calcein for 5 min periods. The IC50 values were obtained by determining the concentration of modulator resulting in 50% of the maximum transport inhibition. Maximum transport inhibition was the % inhibition produced in the presence of 50–60 micromolar verapamil.

Reference Example 3

Fluorescent Substrate Accumulation Assay

NIH-MDR1-G185 cells (obtained from M. Gottesman, NIH) were harvested and resuspended in RPMI-1640 containing L-glutamine, 10% Cosmic Calf Serum and penicillin-streptomycin. Cell suspension aliquots of 175 microliters (1×105 cells) were added to individual wells of a 96 well microtiter plate and preincubated for 15 min at 37° C with 20 microliters MDR modulator diluted in cell culture media to give a final concentration of 10 micromolar. Control wells received no modulating agent. BODIPY-FL Taxol (Molecular Probes, Eugene, Oreg.) was added to each well in 10 microliter aliquots to give a final concentration of 500 nM and cells were incubated for 40 min at 37° C. Cells were centrifuged at 100× g for 5 min at 4° C. and the cell pellet washed with 200 microliters cold PBS to remove fluorescent medium from wells. Cells were centrifuged once more, media removed, and cells resuspended in 200 microliters cold PBS. Fluorescence accumulation was measured in a fluorescence plate reader fitted with an excitation filter of 485 nm and an emission filter of 538 nm. BODIPY-FL taxol accumulation in the cells was calculated as follows:

Accumulation Index=(fluorescence in NIH-MDR1-G185 cells in the presence of modulator)/(fluorescence in NIH-MDR1-G185 cells in absence of modulator)

Reference Example 4

Method for Measuring Substrate Potential for MDR1 (MDR1 ATPase Assay)

Recombinant baculovirus carrying the human MDR1 gene was generated and Sf9 cells infected with virus. The virus-infected cells were harvested and their membranes isolated. MDR1-ATPase activity of the isolated Sf9 cell membranes was estimated by measuring inorganic phosphate liberation as previously described (B. Sarkadi, *J. Biol. Chem.*, 1992, 267:4854–4858). The differences between the ATPase activities measured in the absence and presence of 100 micromolar vanadate were determined as activity specific to MDR1. MDR modulator concentrations causing half-maximum activation (Ka) or half-maximum inhibition of the MDR1-ATPase stimulated by 30–40 micromolar verapamil (Ki) were determined.

Example A

Activity of the Compounds

Accumulation Index of various compounds prepared above was tested according to the method in Reference Example 3. The results are in Table 6.

TABLE 6

Accumulation Index of the Active Compounds

| Compound | Accumulation Index |
| --- | --- |
| (structure) | 2 |
| (structure) | 4 |
| (structure) | 3 |

TABLE 6-continued
Accumulation Index of the Active Compounds
| Compound | Accumulation Index |
|---|---|
| 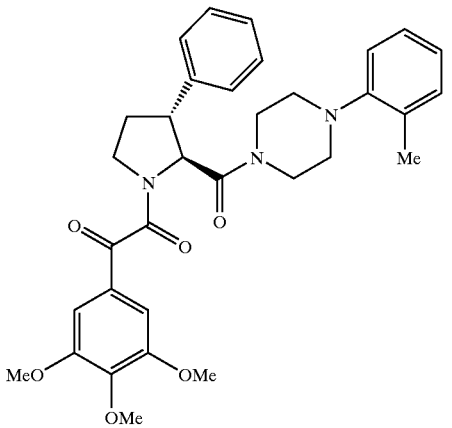 | 6 |
| 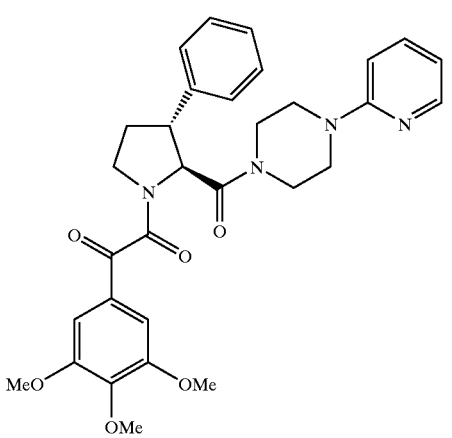 | 5 |
| 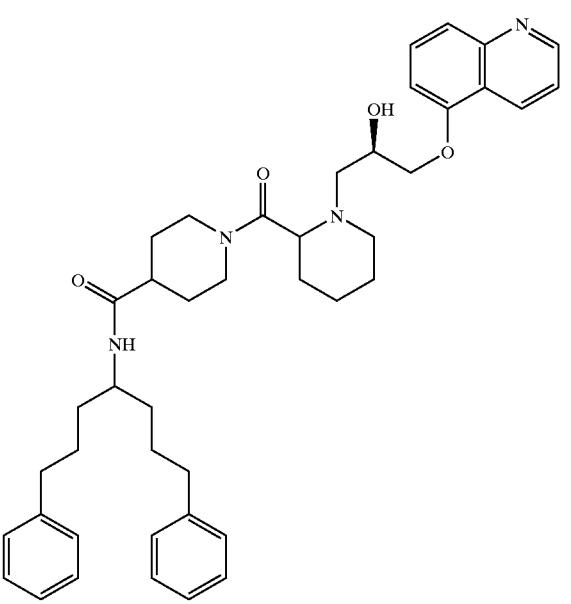 | 9 |

TABLE 6-continued

Accumulation Index of the Active Compounds

| Compound | Accumulation Index |
|---|---|
| 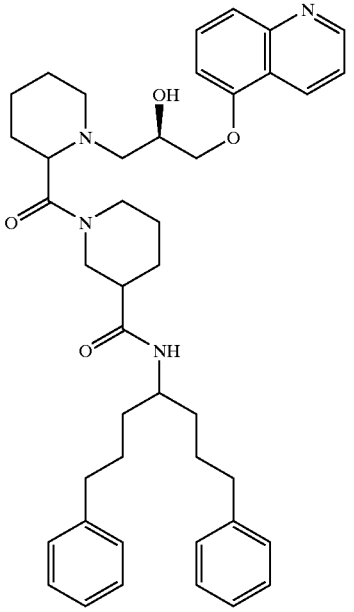 | 9 |
| 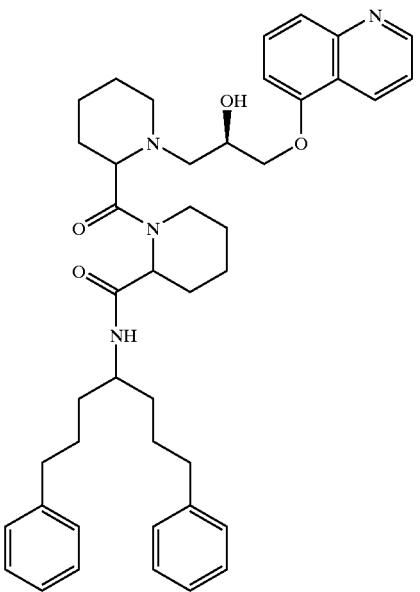 | 11 |

Example B

Oral Composition for the Active Compound of this Invention

A composition for oral administration is prepared by reducing an active compound according to this invention to a No. 60 powder. Starch and magnesium stearate are passed through a No. 60 bolting cloth onto the powder. The combined ingredients are mixed for 10 minutes and filled into a hard shell capsule of a suitable size at a fill weight of 100 mg per capsule. The capsule contains the following composition:

| Active Compound | 5 mg |
|---|---|
| Starch | 88 mg |
| Magnesium Stearate | 7 mg |

Example C

Oral Composition for the Active Compound of this Invention with a Chemotherapeutic Agent A mixture of vinblastine and an active compound of this invention is reduced to a No. 60 powder. Lactose and magnesium stearate are passed through a No. 60 bolting cloth onto the powder. The combined ingredients are mixed for 10 minutes, and then filled into a No. 1 dry gelatin capsule. Each capsule contains the following composition:

| | |
|---|---|
| Active Compound | 5 mg |
| Vinblastine | 5 mg |
| Lactose | 580 mg |
| Magnesium Stearate | 10 mg |

Example D

Parenteral Composition for the Active Compound of this Invention

An active compound according to this invention (1 mg) is dissolved in 1 mL of a solution of 10% cremaphor, 10% ethanol, and 80% water. The solution is sterilized by filtration.

Example E

Parenteral Composition for the Active Compound of this Invention

A sufficient amount of an active compound according to this invention and TAXOL® are dissolved in a 0.9% sodium chloride solution such that the resulting mixture contains 0.9 mg/mL of the active compound of this invention and 1.2 mg/mL TAXOL®.

A sufficient amount of the solution to deliver 135 mg/sq m TAXOL® is administered intravenously over 24 hours to a patient suffering from ovarian cancer.

What is claimed is:

1. A compound having the structure:

or an optical isomer, diastereomer, enantiomer, pharmaceutically-acceptable salt, wherein:
   (a) w is 0 to 6, x is 0 to 10, and t is 0 to 6;
   (b) A is a substituted heterocyclic group having about 4 to about 9 members;
   (c) $R^1$ is selected from the group consisting of a hydrogen atom, a hydroxyl group, a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group,
   (d) $R^2$ and $R^3$ are bonded together to form a substituted piperidyl group;
   (e) $R^4$ is selected from the group consisting of —CH($R^1$)—;
   (f) $R^5$ is selected from the group consisting of —NR$^6$($R^7$)— and —O$_r$R$^6$—; wherein r is equal to 1;
   (g) $R^6$ is selected from the group consisting of a hydrocarbon group, a substituted hydrocarbon group, a heterogeneous group, a substituted heterogeneous group, a carbocyclic group, a substituted carbocyclic group, a heterocyclic group, a substituted heterocyclic group, an substituted aromatic group, a heteroaromatic group, and a substituted heteroaromatic group;
   (h) $R^7$ is selected from the group consisting of a hydrogen atom and $R^6$:
   (i) $R^8$ is selected from the group consisting of a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a substituted heteroaromatic group, and
   (j) $R^9$ is selected from the group consisting of a hydrogen atom or a hydrocarbon group.

2. A compound having the formula:

i)

ii)

or iii)

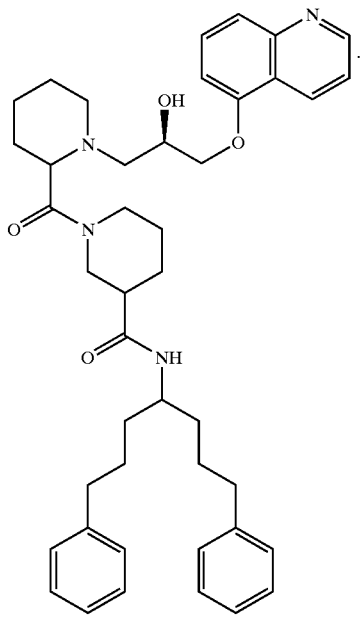

3. A composition comprising:
a) one or more compounds having the formula:

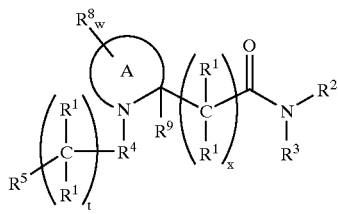

or an optical isomer, diastereomer, enantiomer, pharmaceutically-acceptable salt, wherein:
(a) w is 0 to 6 , x is 0 to 10, and t is 0 to 6;
(b) A is a substituted heterocyclic group having 4 to 9 members;
(c) $R^1$ is selected from the group consisting of a hydrogen atom, a hydroxyl group, a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group;
(d) $R^2$ and $R^3$ are bonded together to form a substituted piperidyl group;
(e) $R^4$ is selected from the group consisting of —CH($R^1$)—;
(f) $R^5$ is selected from the group consisting of —NR$^6$(R$^7$)— and —O$_r$R$^6$—, wherein r is equal to 1;
(g) $R^6$ is selected from the group consisting of a hydrocarbon group, a substituted hydrocarbon group, a heterogenous group, a substituted heterogeneous group, a corbocyclic group, a substituted carbocyclic group, a heterocyclic group, a substituted heterocyclic group, an aromatic group, a substituted aromatic group.
(h) $R^7$ is selected from the group consisting of a hydrogen atom and $R^6$;
(i) $R^8$ is selected from the group consisting of a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, and a substituted heteroaromatic group; and,
(j) $R^9$ is selected from the group consisting of a hydrogen atom or a hydrocarbon group; and,
b) a pharmaceutically acceptable carrier.

4. A method for treating multidrug resistance, said method comprising the step of administering to a human or mammal an effective amount of a composition comprising:
a) one or more compounds having the formula:

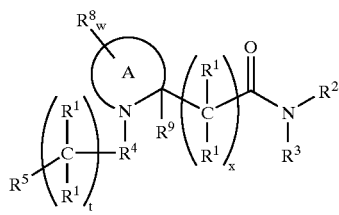

or an optical isomer, diastereomer, enantiomer, pharmaceutically-acceptable salt thereof, wherein:
(a) w is 0 to 6, x is 0 to 10, and t is 0 to 6;
(b) A is a substituted heterocyclic group having 4 to 9 members;
(c) $R^1$ is selected from the group consisting of a hydrogen atom, a hydroxy group, a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group;
(d) $R^2$ and $R^3$ are bonded together to form a substituted piperidyl group;
(e) $R^4$ is selected from the group consisting of —CH($R^1$)—;
(f) $R^5$ is selected from the group consisting of —NR$^6$(R$^7$)— and —O$_r$R$^6$—, wherein r is equal to 1;
(g) $R^6$ is selected from the group consisting of a hydrocarbon group, a substituted hydrocarbon group, a heterogenous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group;
(h) $R^7$ is selected from the group consisting of a hydrogen atom and $R^6$;
(i) $R^8$ is selected from the group consisting of a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, and a substituted heteroaromatic group;
(j) $R^9$ is selected from the group consisting of a hydrogen atom or a hydrocarbon group; and,
b) a pharmaceutically acceptable carrier.

* * * * *